(12) United States Patent
Yankielun

(10) Patent No.: US 6,970,247 B2
(45) Date of Patent: Nov. 29, 2005

(54) METHODS AND DEVICES FOR OPTICALLY RECORDING AND IMAGING REPRESENTATIONS OF INTERACTIONS OF AN OBJECT WITH ITS ENVIRONMENT

(75) Inventor: Norbert E. Yankielun, Lebanon, NH (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 415 days.

(21) Appl. No.: 10/318,129

(22) Filed: Dec. 13, 2002

(65) Prior Publication Data

US 2004/0251405 A1 Dec. 16, 2004

(51) Int. Cl.$^7$ ............................................. G01N 21/00
(52) U.S. Cl. ...................................... 356/436; 385/12
(58) Field of Search ........................... 385/11; 356/436; 250/227.14, 227.21, 573, 576

(56) References Cited

U.S. PATENT DOCUMENTS

| | | | |
|---|---|---|---|
| 4,450,434 A | | 5/1984 | Nielsen et al. |
| 4,714,829 A | | 12/1987 | Hartog et al. |
| 5,191,206 A | | 3/1993 | Boiarski et al. |
| 5,422,495 A | * | 6/1995 | Cohn ........................ 250/573 |
| 5,581,648 A | * | 12/1996 | Sahagen ..................... 385/12 |
| 5,641,230 A | * | 6/1997 | Okubo ....................... 356/339 |
| 5,699,795 A | * | 12/1997 | Richards-Kortum et al. ..... 600/478 |
| 5,771,091 A | | 6/1998 | Paritsky et al. |
| 5,814,524 A | * | 9/1998 | Walt et al. .................... 385/12 |
| 6,016,435 A | * | 1/2000 | Maruo et al. ............... 600/473 |
| 6,130,439 A | * | 10/2000 | Le Menn .................... 250/573 |
| 6,216,540 B1 | * | 4/2001 | Nelson et al. ................ 73/633 |
| 6,239,865 B1 | | 5/2001 | Paritsky et al. |
| 6,678,541 B1 | * | 1/2004 | Durkin et al. .............. 600/476 |
| 2003/0094281 A1 | * | 5/2003 | Tubel ......................... 385/12 |
| 2004/0113104 A1 | * | 6/2004 | Maida, Jr. ................... 250/573 |

* cited by examiner

*Primary Examiner*—Zandra V. Smith
*Assistant Examiner*—Juan D. Valentin, II
(74) *Attorney, Agent, or Firm*—Earl H. Baugher, Jr.

(57) ABSTRACT

Using an array of optical sensors affixed to measure interactions on a surface of an object, in combination with a specially configured personal computer, dynamic mapping of interaction is provided. One application maps washover of an object towed in a large body of water. Data are collected on optical characteristics of the interaction such as reflectivity at a boundary. For example, in one embodiment the reflectivity at an optical fiber/seawater boundary is compared to that of an optical fiber/air boundary and dynamic measurements made using an optical time domain reflectometer (OTDR). These data are then processed using specialized software to yield representation of the dynamics (spatial and temporal) of selected washover events on a surface of interest. The system specifically provides a real-time representation of washover, including two and three-dimensional visualization of washover, as well as recording selected data for future use. Methods of employment of the system are also provided.

32 Claims, 20 Drawing Sheets

METHODS AND DEVICES FOR OPTICALLY RECORDING AND IMAGING REPRESENTATIONS OF INTERACTIONS OF AN OBJECT WITH ITS ENVIRONMENT

STATEMENT OF GOVERNMENT INTEREST

Under paragraph 1(a) of Executive Order 10096, the conditions under which this invention was made entitle the Government of the United States, as represented by the Secretary of the Army, to the entire right, title arid interest therein of any patent granted thereon by the United States. This patent and related ones are available for licensing. Contact Sharon Borland at 703 428-9112 or Phillip Stewart at 601 634-4113.

FIELD OF THE INVENTION

The present invention relates generally to detection of parameters by optical means and more particularly to the real time detecting, recording and presenting representations of interactions with an object, such as a fluid passing over an object.

BACKGROUND

Washover is defined as the condition of occasional (not "frequent," continuous or permanent) partial or complete inundation and exposure of a top surface of a floating object to a fluid. Typically, at sea washover is caused by wave action, wind action, the dynamics of towing a floating object (body) or a combination of the interaction of these factors. Washover may adversely affect performance of floating objects equipped with electronic devices such as antennas, photovoltaic arrays, instrumentation, radio, and auditory or visual beacons. For a low-profile towed body, washover depth is usually within the range of less than a centimeter (0.4") to 30 cm (12"). Typically, an inundation lasts less than one second.

Fiber optic-based methods of the present invention provide three dimensional (3D) spatial and temporal detection, measurement and visualization of washover in both freshwater and seawater and may be applied to other transparent or translucent fluids. Temporal and spatial optical-based washover measurements provide an empirically-based benchmarking process for assessing the computational fluid dynamics of fluid flow around an arbitrarily shaped surface of an object.

A preferred embodiment of the present invention permits simultaneous measurement of temporal and spatial washover dynamics that are non-invasive both physically and electro-magnetically. For example, measurements may be made while taking measurements of water wave/electromagnetic (RF) interaction of onboard electronics, e.g., low profile antennas. Data may be acquired and displayed in real-time, as well as stored for post-processing, analysis, playback and display.

The ability to capture key parameters of washover as data, as well as to visualize washover events in real-time, enables designers to improve hydrostatic and hydrodynamic profiles of these objects. Currently, there are no purpose-built non-interfering devices, systems, or methods that provide this information. Thus, there exists a need for an optical washover measurement system that permits real-time acquisition, three-dimensional mapping, and visualization of seawater washover dynamics without interfering with the operation of onboard electronics. The real-time data acquired with this system may be used to analyze hydrodynamics and electromagnetic interaction with seawater while an electromagnetic device is operating on the object. It is also useful for use in conjunction with computer simulations and modeling to optimize hardware design "off the bench."

A preferred embodiment of the present invention was developed to meet the need to temporally and spatially quantify seawater wave interactions in the VHF through microwave frequency range while electromagnetic energy emanates from a low profile towed body. At these RF frequencies, the skin depth (a measure of the maximum depth to which electromagnetic energy penetrates) is on the order of one centimeter (0.4").

Skin depth, $\delta_s$ (m), is defined as the depth at which a conductor's current is reduced to 0.368 of the surface value, the equivalent to a power loss of 8.7 dB. Doubling the value of $\delta_s$ doubles the loss. Skin depth is frequency dependent, i.e., the higher the frequency, the shallower the skin depth. Skin depth can be defined mathematically as:

$$\delta_s = \sqrt{\frac{2}{\omega \mu \sigma}} = \sqrt{\frac{\rho}{\pi f \mu}} \tag{1}$$

where:

$\mu$=permeability (for seawater, $\mu = 4\pi \times 10^{-7}$ Henrys/m)

$\rho$=resistivity ($\Omega$–m)

$\omega$=radian frequency=$2\pi f$ (Hz)

$\sigma$=conductivity (mho/m)=$\rho^{-1}$, (where mho [$\Omega^{-1}$]=Siemen [S])

FIG. 1 illustrates the frequency dependency of skin depth for two values of resistivity that may be expected for seawater. Across the VHF and UHF spectrum, skin depth is on the order of a couple of centimeters (0.5–0.75") or less and decreases with increasing frequency. For a frequency of 1000 MHz (1 GHz) the skin depth is approximately 0.75 cm (0.3"). Thus, at the preferred higher frequencies even relatively shallow washover has a profound effect on transmitted and received signal levels.

Currently, there are no existing devices, systems, or methods that can provide this information in a non-interfering manner when washover patterns must be studied simultaneously with the evaluation of an onboard electromagnetic antenna or other electromagnetic device. A technique using electrically powered electrodes makes appropriate washover measurements but not on a non-interference basis. U.S. patent application Ser. No. 10/318297, filed Dec. 13, 2002, by Yankielun and Clark. This technique relies on an extensive network of metallic wired electrodes, which interfere with electromagnetic radiation patterns when applied in the immediate proximity of an antenna under test. Accordingly, it may not be used to perform non-interfering measurements simultaneously with operation of onboard electronics.

A preferred embodiment of the present invention uses opto-electronic techniques to provide a method and apparatus that facilitates real-time acquisition of pertinent parameters to enable two or three-dimensional mapping and visualization of washover. In a specific application, it provides an empirically based benchmarking process for computational fluid dynamic assessments of turbulent flow around arbitrarily shaped surface-towed bodies.

SUMMARY

A system detects, measures and records interaction of an object with its environment, in particular, fluid washover of an object, including displaying a representation thereof in real time. In one embodiment, it uses optical fiber arranged to form an array of separate optical sensors to measure the interaction on the external side of a surface of interest of the object. The configuration of the array, i.e., spacing between each sensor and overall size, is chosen to complement the pulse width, and possibly the pulse repetition frequency, of the light source and to provide a pre-specified level of detail needed for display. The configuration of individual optical sensors in the array may be by way of individual optical fibers inserted through the surface, T-connectors, Y-connectors, simple loops of a single fiber exposed to ambient conditions above the surface, or like means. Ambient light or a separate light source providing modulated pulsed light through a separate optical fiber may be used to operate the system. Further, a single optical fiber may be employed for transmitting and receiving light from all sensors used in the system. An optical fiber, or fibers, provides feedback on sensor status to a signal conversion, collection, processing, recording and display sub-system, e.g., a personal computer (PC) loaded with appropriately configurable software and equipped with a monitor and an optical to digital electronic (O/E) data converter/collector/processor, such as a multi-channel multiplexed printed circuit board incorporating a phototransistor, and an analog-to-digital (A/D) converter.

The sub-system collects (captures) data representing the sampling of at least one optical characteristic at each sensor in the array. The optical characteristic chosen for measurement may be any of the following: wavelength, pulse width, amplitude, phase, phase delay, modulation, and any combination thereof.

The optical fibers may be any of various types of flexible, robust, plastic, optical fiber that may be inserted through the outer surface of the object to be tested. The means for insertion include drilling holes through the appropriate portion of the outer surface to accommodate a tight fit of a T- or Y-connection of an optical fiber "stub" or "lacing" a continuous optical fiber through an array of holes drilled in the surface to form an optical path. If a lacing arrangement is used, the optical fiber exposed on the outer surface is separated from any opaque cladding so that light may be received by each of the exposed loops. The return signal from each sensor in the array is converted to an electrical signal at a phototransistor, converted from analog to digital format and further processed for immediate display or stored for future use. The optical fiber sensors may also be embedded in a thin flexible (conformable) panel, i.e., a panel <0.25 cm (0.1") thick at its greatest depth. This thin conformable panel configuration enables non-destructive testing of an object while minimizing any disruption to washover patterns at the surface being measured.

An embodiment of the present invention envisions the fluid to be a liquid with the object floating in the liquid such that a part of the object is free from contact with the liquid when the liquid is not acted on by external forces. A specific embodiment displays a dynamic representation of seawater washover of a towed body.

Also provided is a method for using a preferred embodiment of the present invention. The method for detecting, measuring and recording interaction of an object with its environment, such as fluid washover of an object, includes displaying a representation of the interaction in real time. It is accomplished by providing an array of exposed optical fibers upon a surface of interest. In its most basic embodiment, each exposed optical fiber is separately provided to the surface of interest. In one embodiment the array may be mounted to the external side of a surface of interest of said object via waterproof gasketed through-holes by either a T- or Y-connector to a stub optical fiber that serves as an individual fiber optic sensor in any array that is fed by one optical fiber connected to a common light source and data collector. In another embodiment a single optical fiber may be woven through an array of watertight gasketed holes in the surface, thus providing a single path for data to be acquired using a suitable means, such as a time domain multiplexer (TDM). The loops on the external surface that are formed by the weaving are stripped of any opaque cladding and serve as the individual sensors in the array. By pulsing light through the fiber optical cable, and any of the stubs in certain configurations, specific optical characteristics are collected as data during selected washover events. These characteristics are selected based on the likelihood of variation based on the amount and timing of fluid accumulating over each individual sensor in the array. These data are converted from light pulses to electrical pulses and further processed. Selected data are either displayed in real time, recorded for later use, or both. This method enables visualization of representations of selected washover events via a real time display as well as recording selected representations of washover events for future use. Optical characteristic that may be measured include: wavelength, pulse width, amplitude, phase, phase delay, modulation, and any combination thereof.

A preferred method involves pulsing light at a pulse width that enables pre-specified parameters of washover to be monitored. In a preferred embodiment, the pulsed light signal is modulated to distinguish changes in ambient lighting from changes due to washover. In a preferred embodiment, this method is used to determine washover of a liquid with the object floating therein such that only part of the object is covered with the liquid when the liquid is not acted on by external forces. In a specific application, the object is a towed body that may be washed over by seawater.

Further, a preferred embodiment of the present invention may be implemented in a simulator such that an expensive object of interest is simulated by a model that mimics its shape, center of gravity, mass, orientation, etc. The model may be provided as a full-scale or partial scale replica of the object with the configuration of the optical sensor array scaled accordingly.

In another preferred embodiment, a "distributed sensor" arrangement employing the principles of optical time domain reflectometry (OTDR) uses a single optical fiber with either T- or Y-connectors to the individual sensors in the array. By measuring the roundtrip time for a light pulse to travel to each of the sensors in the array and also reflect from the termination of the optical fiber, values for operation in a pre-specified quiescent state, e.g., dry ambient air, may be collected and used as a reference to various conditions of washover and may even be used to determine the composition of washover, e.g., seawater, ice, snow, fog, steam, etc.

Implementation of a preferred embodiment of the present invention provides continuous non-interfering, real-time acquisition, processing, mapping and visualization of washover events for military, industrial, and commercial users. It uses a fiber optic array to provide continuous, real-time mapping and visualization of washover. It specifically provides real-time spatial and temporal visualization of washover, including two and three-dimensional visualization of washover. Some applications include:

a physically and electromagnetically non-interfering tool for hydrodynamic and hydrostatic evaluation of a body subjected to washover;
general surface flooding applications;
wave height gauging when applied in a vertical format;
a tool for optical, auditory, and visual performance evaluation of a body subjected to washover; and
objective real-time evaluation of towed body washover, hull hydrodynamic performance, buoy and tethered body hydrodynamics, and vessel superstructure washover even while operating in the electromagnetic spectrum.

There are several general advantages to the implementation of a preferred embodiment of the present invention in any of the above applications:

non-interference with normal operation of the device in the electromagnetic spectrum;
simple to implement for bench testing, i.e., may be implemented as a single shared, non-multiplexed signal path rather than multiplexed, switched, or multiple signal paths, one for each sensor;
inexpensive to implement, operate, and maintain;
collects washover data in real-time;
requires minimal training of system installers, operators, and maintenance personnel;
adaptable to various shapes;
provides visualization in both real-time and after processing collected data;
may incorporate a single optical fiber path from sensor to instrumentation, thus no multiplexer electronics required;
no power is needed to be supplied to towed body, simplifying design; and
fiber optics does not rely on water conductivity for this technique to function.

DETAILED DESCRIPTION

Optical systems and methods for measuring the interaction of an object with its environment are provided. In a preferred embodiment of the present invention, optical systems and methods for measuring washover thickness of seawater, i.e., "washover mapping," are provided.

A preferred embodiment of the present invention acquires and records the changing reflectance levels at known lengths along an optical fiber (cable) as a function of a change in the refractive index contrast of light in any of the visible, IR, and UV spectra at the boundary of the optical fiber path and the overlying composition, e.g., air or seawater. If the optical fiber is exposed to air, there will be a specific and measurable level of reflectance. If instead, the optical fiber were to be exposed to seawater (as would occur during washover) a different level of reflectance is measured. By noting the difference between reflectance levels occurring with air and seawater, washover may be monitored dynamically by taking samples at appropriate pre-specified levels according to the needs of the user.

The combination of several fundamental properties of optics, including Snell's Law, and the concept of geometric spreading is exploited to enable dynamic detection, measurement, and display of washover. For further reference see: Allard, F. C., *Fiber Optic Handbook for Engineers and Scientists*, McGraw-Hill, N.Y., 1990, and Udd, E., *Fiber Optic Sensors: An Introduction for Engineers and Scientists*, Wiley, N.Y., 1990.

Figure 1:
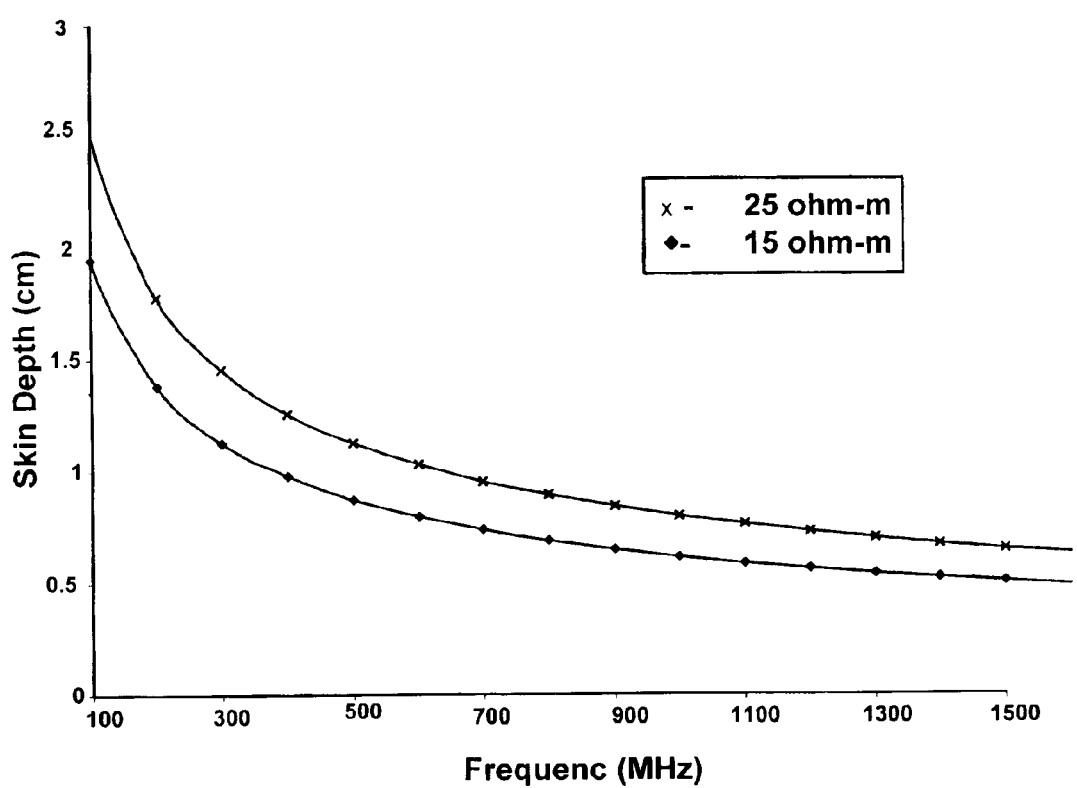
FIG. 1 depicts the relationship between skin depth and frequency for two values of seawater resistivity.
Figure 2:
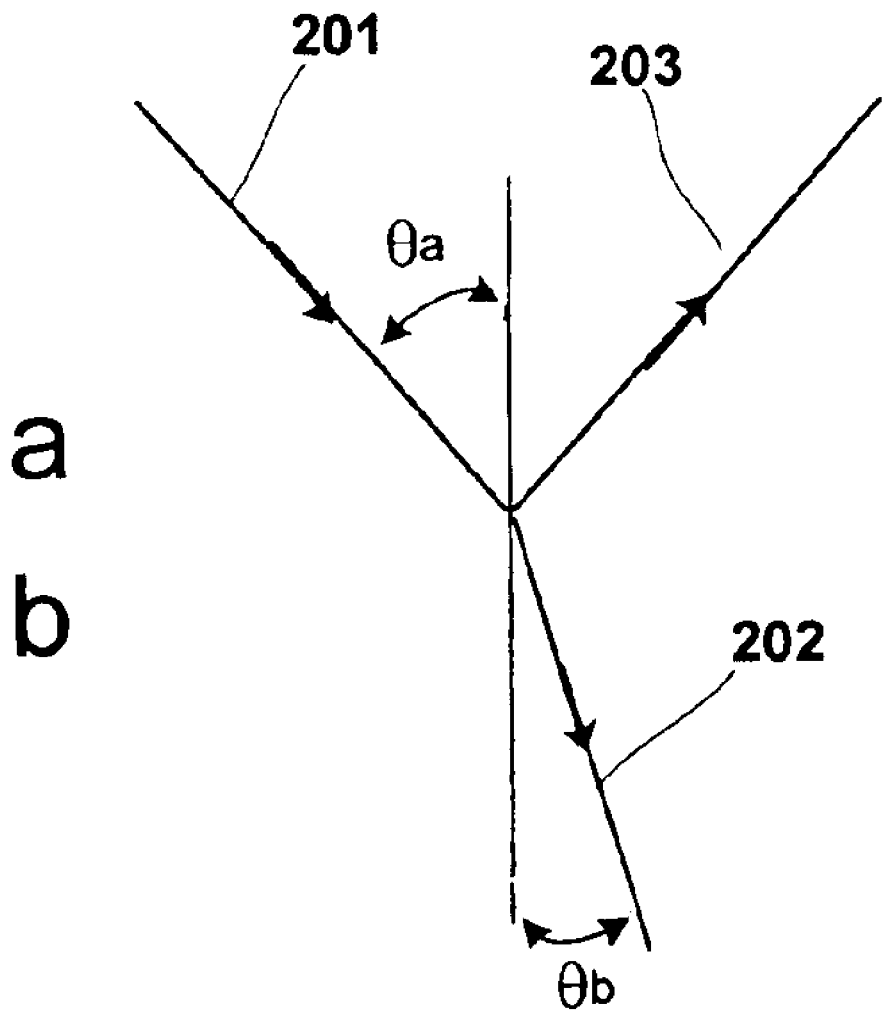
FIG. 2 is a graphic useful for understanding Snell's Law.

Refer to FIG. 2. The primary concept employed in this technique relies on Snell's Law, where at an arbitrary refractive index interface boundary, ab, a first fraction 202 of the energy enters the material from a to b, and the reflection coefficient, $\rho_{ab}$, represents the second fraction 203 of the total energy 201 incident on the boundary ab that is reflected. The reflection coefficient, $\rho_{ab}$, is defined as:

$$\rho_{ab} = \left| \frac{\eta_a \cos(\theta_b) - \eta_b \cos(\theta_a)}{\eta_a \cos(\theta_b) + \eta_b \cos(\theta_a)} \right| \quad (2)$$

where:

$\eta_a$=refractive index of first material, a, at the interface boundary $\eta_b$=refractive index of the second material, b, at the interface boundary $\theta_a$=incident angle, with respect to vertical $\theta_b$=refractive angle, with respect to vertical.

Under Snell's law, light incident at a normal (90° to the surface) incident angle, i.e., the angle at which $\theta_a$ goes to zeros has the associated normal refractive angle $\theta_b$=0, such that the reflection coefficient for a normal incident wave upon an arbitrary refractive index boundary discontinuity results in:

$$\rho_{ab} = \left| \frac{\eta_a - \eta_b}{\eta_a + \eta_b} \right| \quad (3)$$

Complementing the reflection coefficient is the transmission coefficient, $\tau_{ab}$, representing the fraction 202 of light energy that passes through the refractive index boundary, given as:

$$\tau_{ab} = 1 - \rho_{ab} \quad (4)$$

Thus, the fraction 203 of incident energy that is reflected is dependent on the relative magnitudes of the refractive index of the two materials that meet at an interface boundary. To monitor or measure washover, the value of $\eta_a$ is fixed as the refractive index of the fiber optic transmission medium. A plastic optical fiber core has a nominal index of refraction of $\eta_a$=1.492. The value $\eta_b$ will vary with the overlying composition, e.g., for a towed body in seawater it would be either of the discrete values of 1 (air) and 1.3 (nominal for seawater).

In the case of washover measurement, there are three distinct refractive index boundary cases. When the optical fiber is submerged by washover there are two boundaries to consider: an optical fiber/water boundary and a water/air boundary, each of which have associated reflection coefficients. When there is no washover present, there will be only one boundary of concern: an optical fiber/air boundary.

Figure 3:
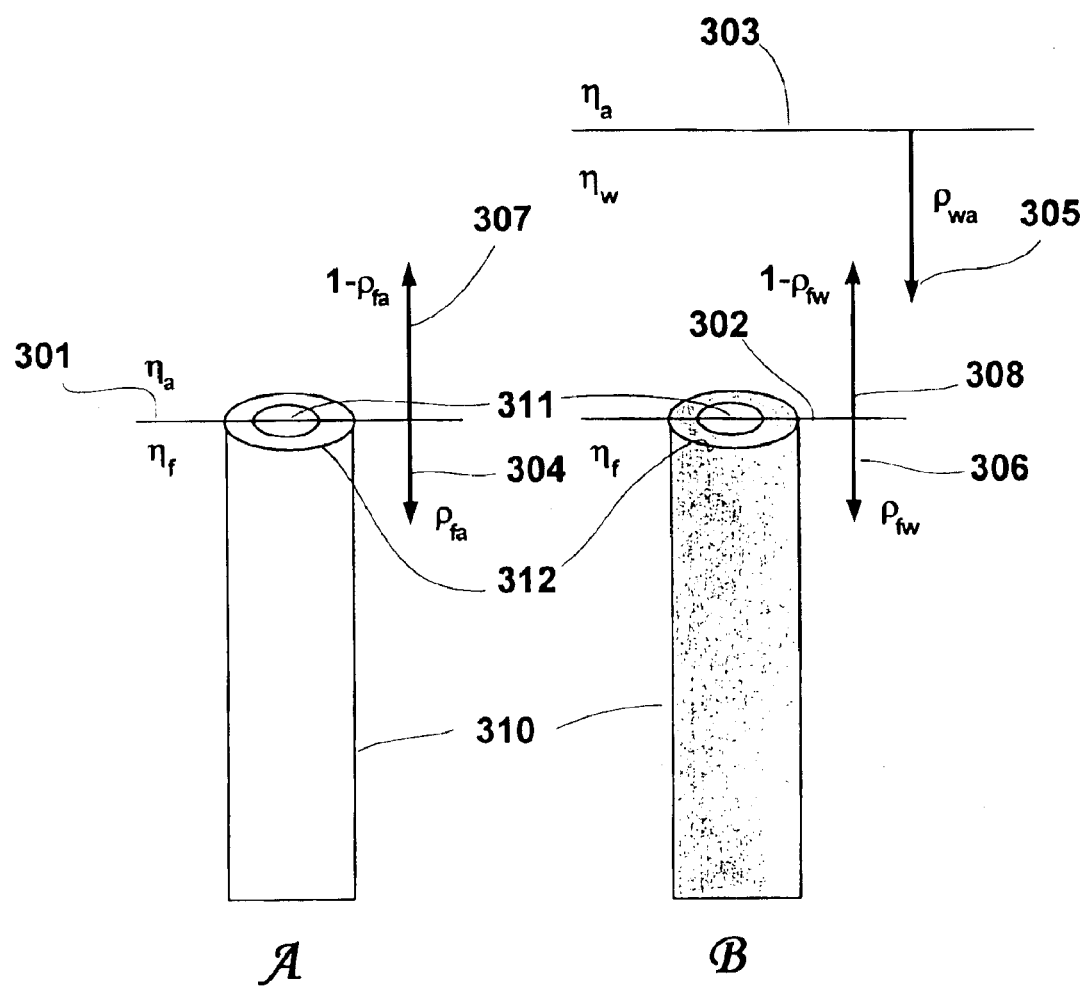
FIG. 3A is a representation of light propagation from an optical fiber through, and reflection from, a single boundary between different materials.
FIG. 3B is a representation of light propagation from an optical fiber through, and reflection from, two boundaries between three different materials.

Refer to FIG. 3. FIG. 3A represents the one-boundary case (optical fiber/air) 301 of no washover and FIG. 3B represents the two-boundary case (optical fiber/water 302, water/air 303) of washover. For the one-boundary case 301, the fraction 307 of light reflected back at the air/water interface is dependent on one coefficient, $\rho_{fa}$. At the water/air boundary 303, the fraction 305 of the incident light associated with the coefficient, $\rho_{wa}$, reflected back down through the water is also of interest together with the fraction 306 of light associated with the coefficient, $\rho_{fw}$. Of course, the fraction 307 of light associated with the coefficient, $1-\rho_{fa}$, that is emitted into free space in FIG. 3A is of no concern. However, as discussed further below, the fraction 308 of light associated with the complementary coefficient, $1-\rho_{fw}$, that continues from the fiber optic/water interface 302 during washover must be taken into consideration since it also continues to the air/water interface 303. For nominal values of seawater, the reflection coefficient, $\rho_{wa}$, at the water/air boundary is:

$$\rho_{wa} = \left| \frac{\eta_w - \eta_a}{\eta_w + \eta_a} \right| = 0.130 \quad (5)$$

where:

$\eta_w$=nominal refractive index of seawater and $\eta_a$=refractive index of air.

At the optical fiber/water boundary 302, the fraction 308 of light transmitted through this boundary 302 and up into the overlying water column is of interest. For nominal values of seawater, the reflection coefficient, $\rho_{fw}$, at the optical fiber/water boundary 302 is:

$$\rho_{fw} = \left| \frac{\eta_f - \eta_w}{\eta_f + \eta_w} \right| = 0.069 \quad (6)$$

where:

$\eta_w$=nominal refractive index of seawater and $\eta_f$ = nominal refractive index of the core of a plastic optical fiber.

Thus, the transmission coefficient is $\tau_{fw}=1-\rho_{fw}=0.931$.

At an optical fiber/air boundary 301, of interest is the fraction 304 of light reflected back from that boundary 301 into the optical fiber 310 since there is no other reflecting boundary overhead. In this case, i.e., no washover present, the reflection coefficient, $\rho_{fa}$, at an optical fiber/air boundary 301 is:

$$\rho_{fa} = \left|\frac{\eta_f - \eta_a}{\eta_f + \eta_a}\right| = 0.192 \qquad (7)$$

where:

$\eta_f$ = nominal refractive index of the core of a plastic optical fiber and $\eta_a$ = refractive index of air.

For light emitted from the small aperture 311 at the end of an optical fiber 310 the power per unit area or irradiance, I, in the direction of propagation of a spherical wavefront of light varies inversely as the square of the distance, r, from the source aperture, such that:

$$I \propto \frac{1}{r^2} \qquad (8)$$

Figure 4:
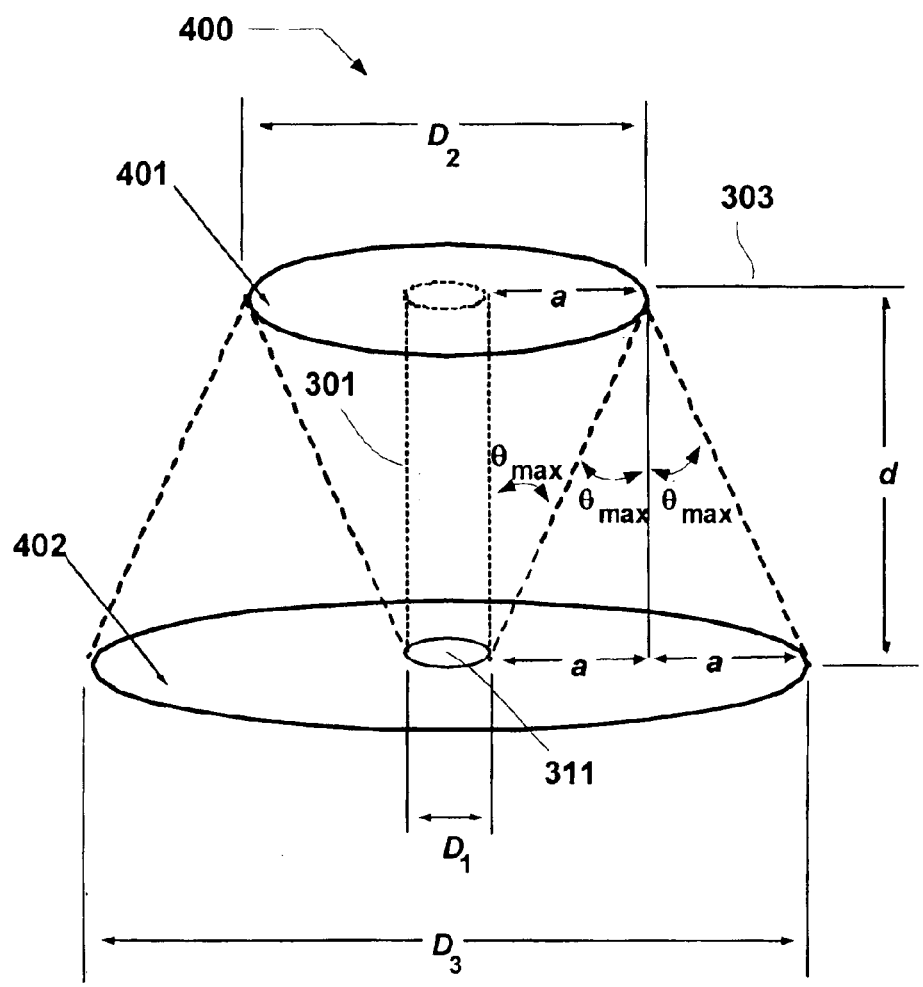
FIG. 4 depicts light reflection footprints for a single sensor used in a preferred embodiment of the present invention.

Refer to FIG. 4. Using the above principles and a geometric representation 400 of the illuminated 401 and reflected 402 footprints of light emitted by a fiber optic aperture 311 submerged below a certain depth, d, of water, a relationship between depth, d, and received light signal intensity can be developed. $D_1$ is the diameter of the fiber optic aperture 311. $D_2$ is the diameter of the illuminated footprint 401 at the water/air interface 303. $D_3$ is the diameter of the footprint 402 from the light reflected back to the plane of the optical fiber aperture 311 from the water/air interface 303. The angle, $\theta_{max}$, is the maximum angle for the optical fiber to collect light. It is the maximum angle through which light can enter or leave the optical fiber aperture 311 of a step index optical fiber. This value, called the numerical aperture, NA, is provided by the optical fiber manufacturer and can be described by:

$$NA = \sin\theta_{max} = \sqrt{\eta_{co}^2 - \eta_{cl}^2} \qquad (9)$$

where $\eta_{co}$ = optical fiber core refractive index and $\eta_{cl}$ = optical fiber cladding refractive index.

The area, $A_1$, of the optical fiber aperture 311 is given by:

$$A_1 = \pi\left(\frac{D_1}{2}\right)^2 \qquad (10)$$

The area of the of the water/air boundary reflection footprint 402, $A_2$, is given by:

$$A_2 = \pi\left(\frac{D_2}{2}\right)^2 = \pi\left(\frac{D_1 + 2a}{2}\right)^2 \qquad (11)$$

where $D_2$ = diameter of the illuminated footprint 401, where $$a = d\tan\theta_{max}. \qquad (12)$$

The diameter $D_3$ of the reflected footprint 402 in the plane of the optical fiber aperture 311 is given by:

$$D_3 = D_1 + 4a. \qquad (13)$$

The area, $A_3$, of the reflected footprint 402 in the plane of the optical fiber aperture 311 is:

$$A_3 = \pi\left(\frac{D_3}{2}\right)^2 = \pi\left(\frac{D_1 + 4a}{2}\right)^2. \qquad (14)$$

For an optical fiber aperture 311 submerged beneath a depth, d, of water, the reflected signal intensity, $S_i$, at the optical detector (e.g., the photo transistor 810 of FIG. 8), relative to the source (e.g., the red LBD 801 of FIG. 8), is the ratio of the area, $A_1$, of the aperture 311 of the optical fiber to the area, $A_3$, of the reflection-illuminated footprint 402 in the plane of the fiber aperture 311 multiplied by $\rho_{wa}$ and $\tau_{fw}$ such that:

$$S_i = \frac{A_1 \rho_{wa} \tau_{fw}}{A_3} \qquad (15)$$

Figure 5:
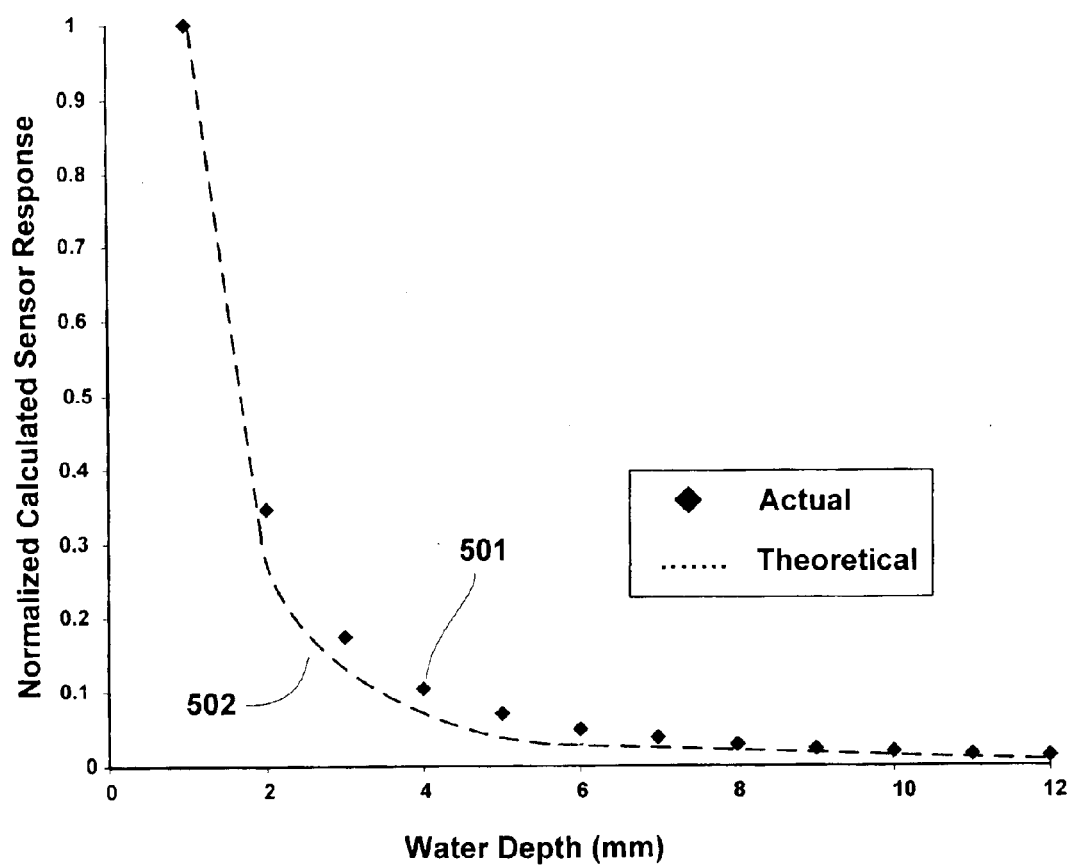
FIG. 5 depicts the relationship between normalized calculated optical sensor response for an optical sensor of the present invention and water depth, i.e., a calibration curve, as compared to the theoretical $1/r^2$ falloff relationship.

Refer to FIG. 5, comparing a normalized plot 501 of Eqn. (15) for a water depth range of 0 to 12 mm (0.47") to a theoretical $1/r^2$ falloff curve 502. For an optical fiber aperture 311 exposed to air, the reflected signal intensity at the optical detector 810, relative to the source 801, is proportional to $\rho_{fa}$ as defined in Eqn. (7).

Figure 6:
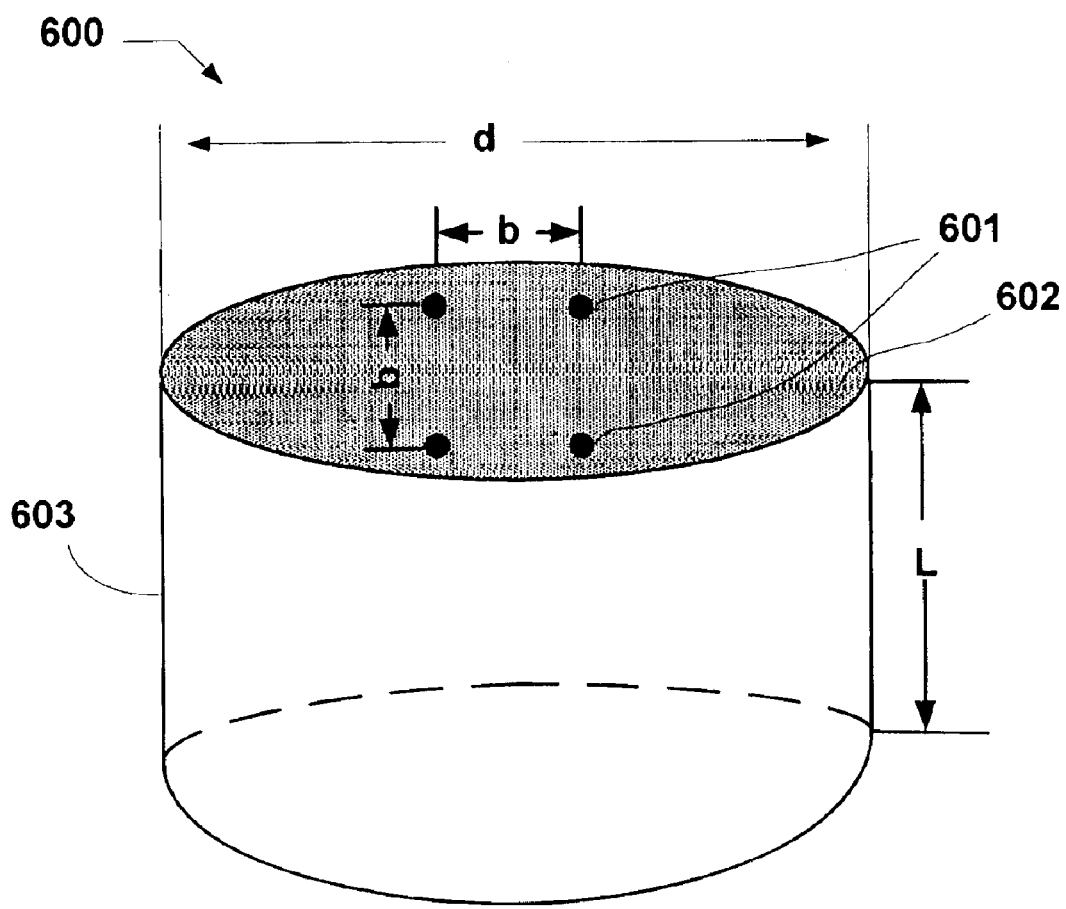
FIG. 6 is a diagram of a cylinder to which an array of optical sensors is attached at one end for use in testing an embodiment of the present invention.

Refer to FIG. 6. In a specific test, a fiber optic washover sensor array test cylinder 600 consists of an array of four single point optical fiber (cable) terminations 601 appearing flush with the top (closing) surface 602 of a PVC pipe cap 603 of diameter d and depth L. For this test, the PVC cap 603 was 10 cm (4") in external diameter by 7.5 cm (3") deep. Four fiber optic terminations 601 are centered in the bottom 602 of the capped cylinder 603 (PVC cap) and form the corners of a square with a dimension of b. For this application, b=5 cm (2"). The optical fiber used for this application is a one mm, step index plastic optical fiber with a numerical aperture, NA, of 0.51, a core refractive index, $\eta_{co}$, of 1.492, a cladding refractive index, $\eta_{cl}$, of 1.402, and an attenuation of <0.20 dB/m.

Figure 7:
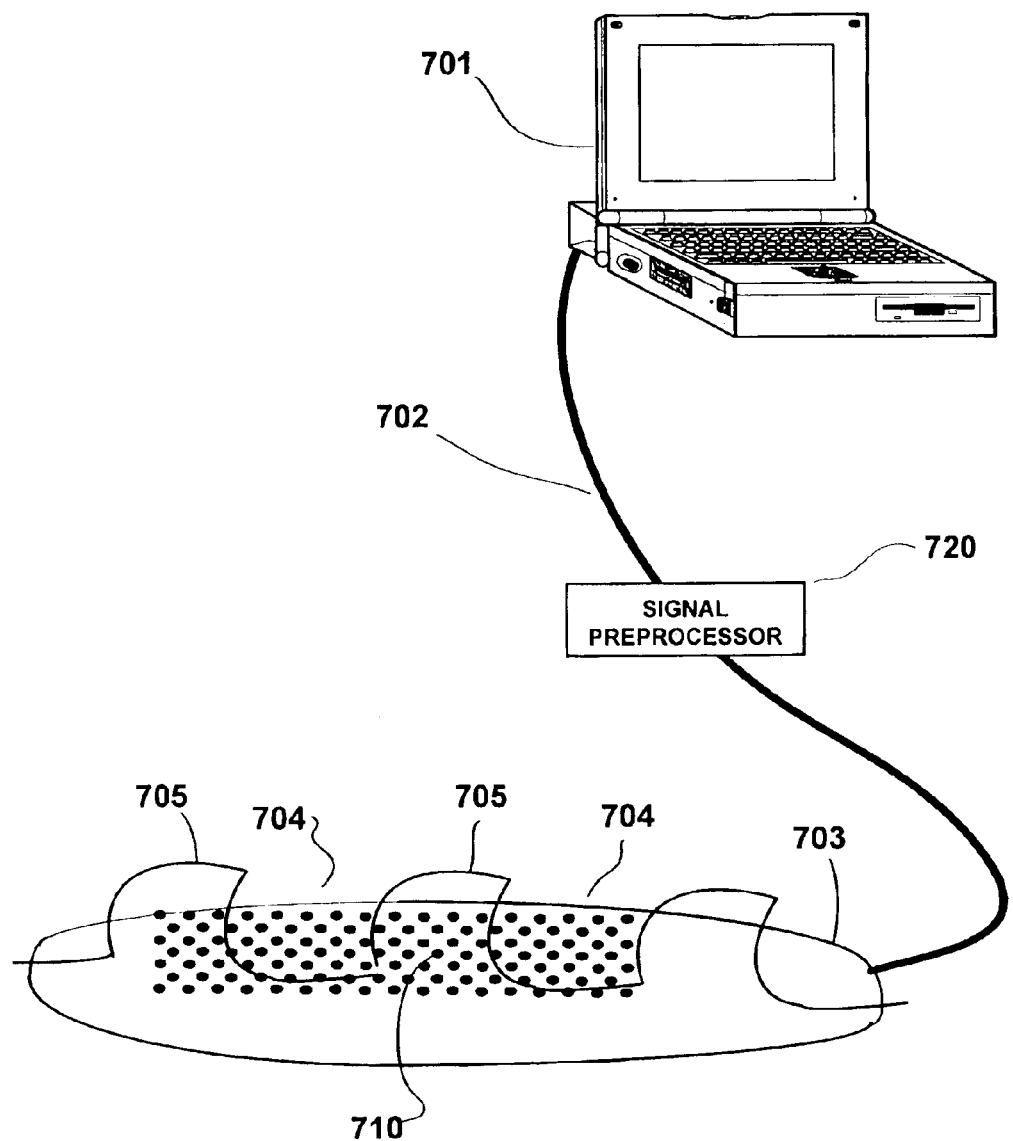
FIG. 7 depicts a preferred configuration for taking data characterizing washover from an object experiencing washover while the object is operating in the electromagnetic spectrum.
Figure 8:
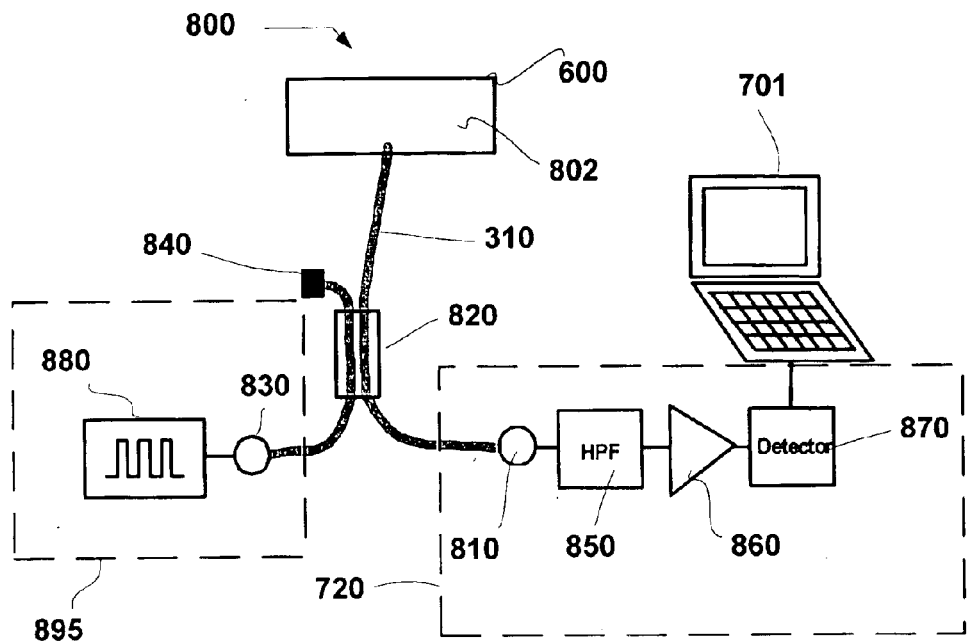
FIG. 8 is a schematic of the major optical and electrical portions of a preferred embodiment of the present invention as used in taking data from a single optical sensor.

Refer to FIG. 7 showing a relational diagram of a test configuration for a towed body 703 and FIG. 8 depicting the electronic schematic 800 for connections to a single sensor such as the sensor 601 in an array as may be configured in a laboratory. Each fiber optic cable 310 is connected to a directional optical coupler 820.

Figure 10:
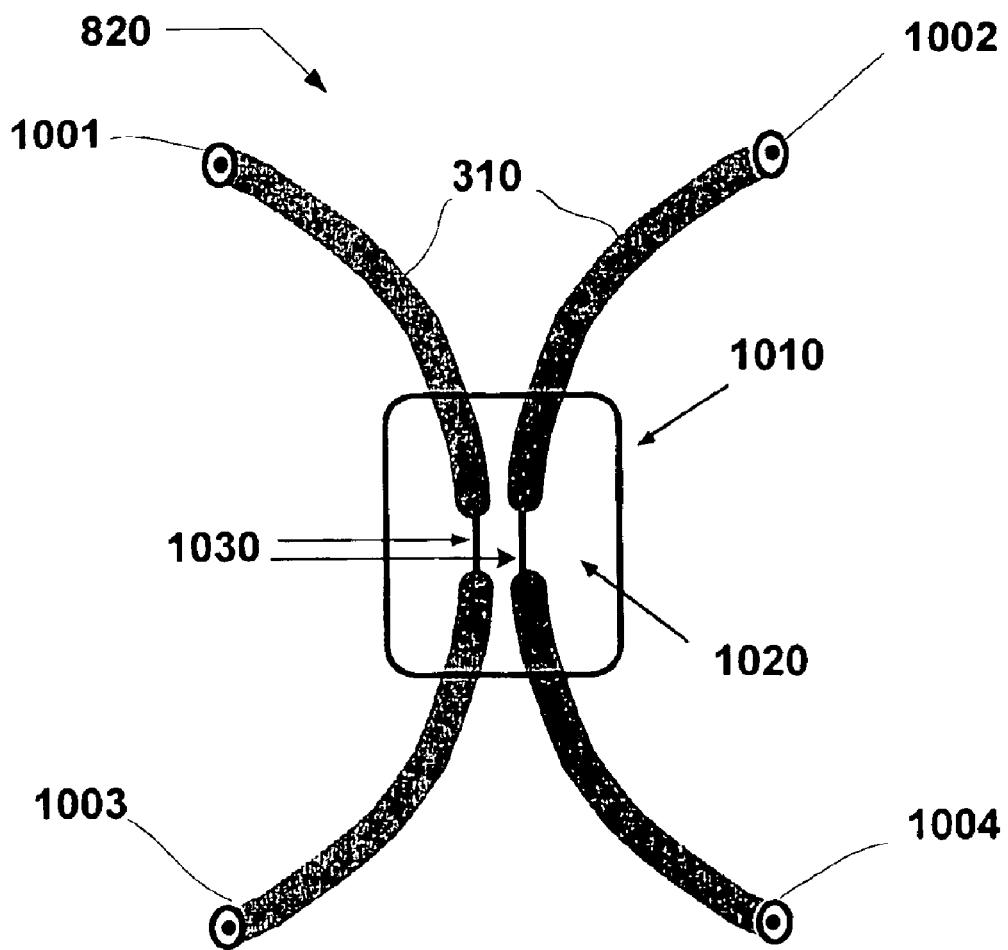
FIG. 10 is a representation of a fiber optic directional coupler used in a preferred embodiment of the present invention.

Refer to FIG. 10 for a diagram of a directional fiber optic coupler 820. At the coupler body 1010, each of the two optical fibers associated with the four ports 1001–1004, are stripped of their cladding within the coupler body 1010 as depicted at 1030. The stripped sections are embedded in a stabilizing material 1020 to assure maintenance of the correct orientation. Light energy entering Port 2 1002 is divided in half with equal components exiting through Ports 3 1003 and 4 1004. Virtually no light entering Port 2 1002 exits through Port 1 1001. The coupler 820 functions similarly for light entering any of the four ports 1001–1004. The coupler 820 permits a single optical fiber 310 to act simultaneously as a receiver and a transmitter.

Refer to FIGS. 8 and 10. The first port 1001 of the coupler 820 is a dark termination 840 implemented by covering the aperture 311 with black plastic tape. A second port 1002 for inputting light to the system is terminated in the test cylinder 600 shown from its side 802. An optical receiver 810, such as a phototrarisistor, is connected to a third port 1003 of the coupler 820. To complete the connections, a visible light source 830, e.g., a 660-nm red LED, is connected to a fourth port 1004. Each of the four optical sensors 601 in the array of FIG. 6 is configured similarly.

Since the present invention is used under a variety of ambient light conditions, this "background" light is sensed by the phototransistor 810 (or power meter in an alternate configuration) and, without further accommodation, interferes with accurate measurements. This period of notable change in light intensity as sensed by the phototransistor 810 may be on the order of seconds. Refer to FIG. 7. Additionally, this change in ambient light may occur during washover 705 of the installed sensor array 710, during which time the ambient light is also partially attenuated by the washover fluid, e.g., water, and the changing ambient light may give a false reading as to those portions 704 of the object 703 not being inundated. Note that portions 704 not affected by wave action washover 705 should remain at the quiescent level used as a reference.

The variation of ambient light intensity (from the sun, moon, stars, lightning, artificial lighting, or a combination thereof) due to changing cloud cover, for example, is a relatively slow process. Further, in an artificially lit environment, such as in the laboratory, the fluorescent or incandescent lighting generates light intensity fluctuation at 120 Hz that may interfere with the expected response of an optical sensor if the response is not augmented with appropriate signal conditioning. Thus, to eliminate interference from all types of ambient lighting, a modulating signal such as a 3-kHz square wave source 880 is used to modulate the signal from the red LED 830. The signal received by each phototransistor 810 is input to a high-pass filter 850, eliminating low-frequency components of the signal and permitting "cleaner" analog processing of the received 3-kHz modulated signal. This filtered signal, now frequency down converted to a radio frequency (RF) from an optical frequency, is then passed to an amplifier 860 from which the amplified signal is peak rectified in a detector 870, resulting in a DC voltage proportional to the intensity of the received modulated LED light. The output of the detector 870 is digitized, e.g., using a 16-bit PCMCIA analog-to-digital (A/D) converter card (not shown separately) installed in a laptop computer 701. The subsequent data stream is processed in accordance with pre-specified user requirements, and either stored for later use, displayed in real time, or both.

Figure 9:
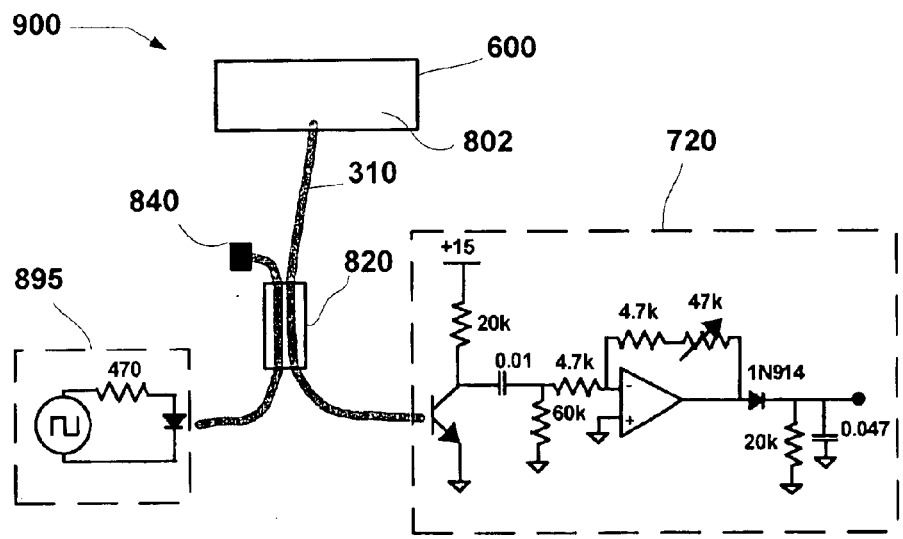
FIG. 9 is a schematic of specific optical and electrical portions of a preferred embodiment of the present invention as used in taking data from a single optical sensor.

Refer to FIG. 9 for one example of specific circuitry 720, 895 to accomplish the modulation of the source LED 830 and preprocessing (conversion) (O/E) 720 of the optical signal to an RF (electronic) signal usable by the specially configured PC 701.

Figure 11:
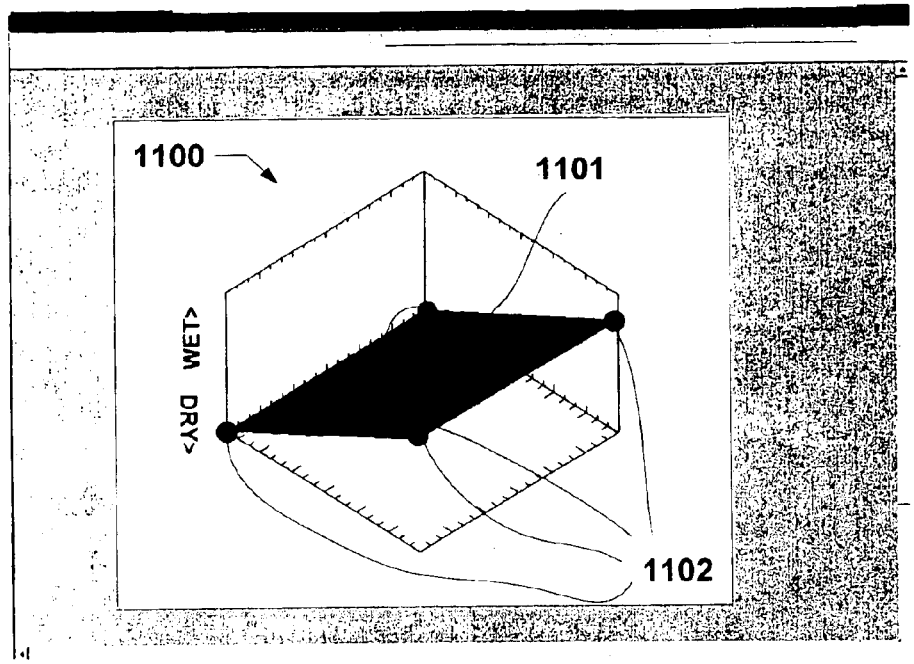
FIG. 11 is a screen image of output data processed by a laptop computer from a laboratory experiment using a four-sensor array and connected processor electronics that may be employed in an embodiment of the present invention.

Refer to FIG. 11. For a specific test, the data acquisition, processing and display software may be written in LABVIEW®, a graphical user interface (GUI)-based language. Two display formats may be created for visualization of the real-time dynamic washover data. FIG. 11 provides a "snap shot" sample 1100 of test data as an analog representation of washover. It is displayed as a three-dimensional (3D) graph 1100 of a dynamically changing rectangular plane 1101 with corner points 1102 (exaggerated for illustration only) representing the location of the four optical sensors (optical fiber terminations) 601 used in the configuration 600 of FIG. 6.

Figure 12:
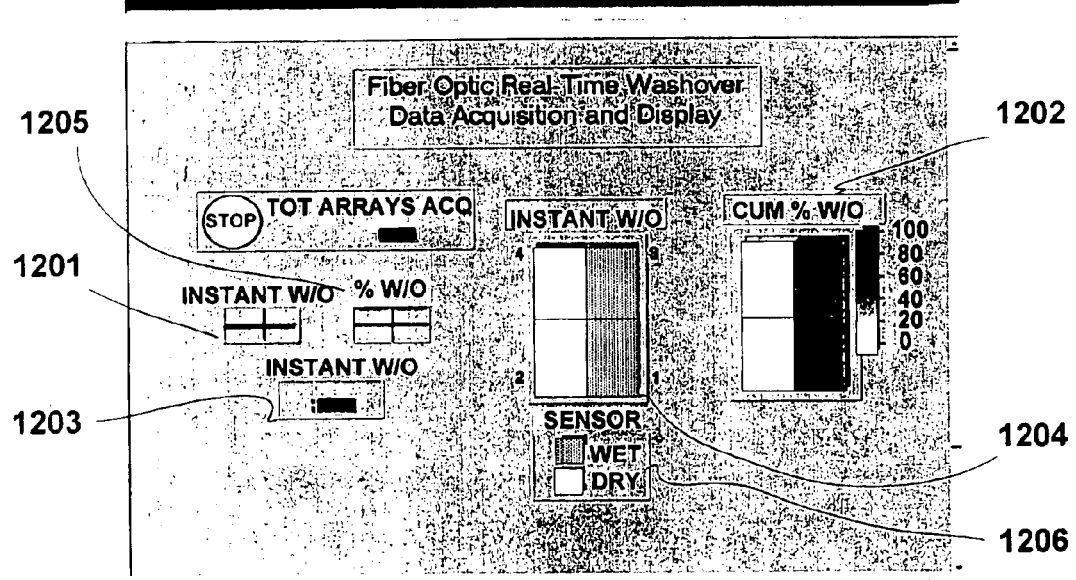
FIG. 12 is a screen image of a four-sensor laboratory experiment that provides processed data in a number of different graphic and non-graphic formats.

Refer to FIG. 12. As further demonstration of how washover data may be presented, a display 1200 provides a binary representation in alphanumeric 1201 and graphical 1202, 1204 format of the washover state relative to a monitored threshold 1203. The threshold 1203 may be set to a predefined depth. Above that depth the status 1206 is defined as wet; below that depth, it is defined as dry. A real-time display 1204 of washover state (wet or dry) is graphically presented as well as a statistical representation 1205 of the percent of time that the four-sensor array of FIG. 6 has been inundated during a given period of interest.

Test Results

Refer to FIG. 6. To illustrate the real-time dynamics of a preferred embodiment of the present invention, a test cylinder 600 was filled with seawater to a depth of approximately 0.5 cm (0.2"). The cylinder 600 was manually rotated and tilted at an angle permitting the water level to vary and sequentially submerge and expose elements 601 in a sensor array.

Figure 13:
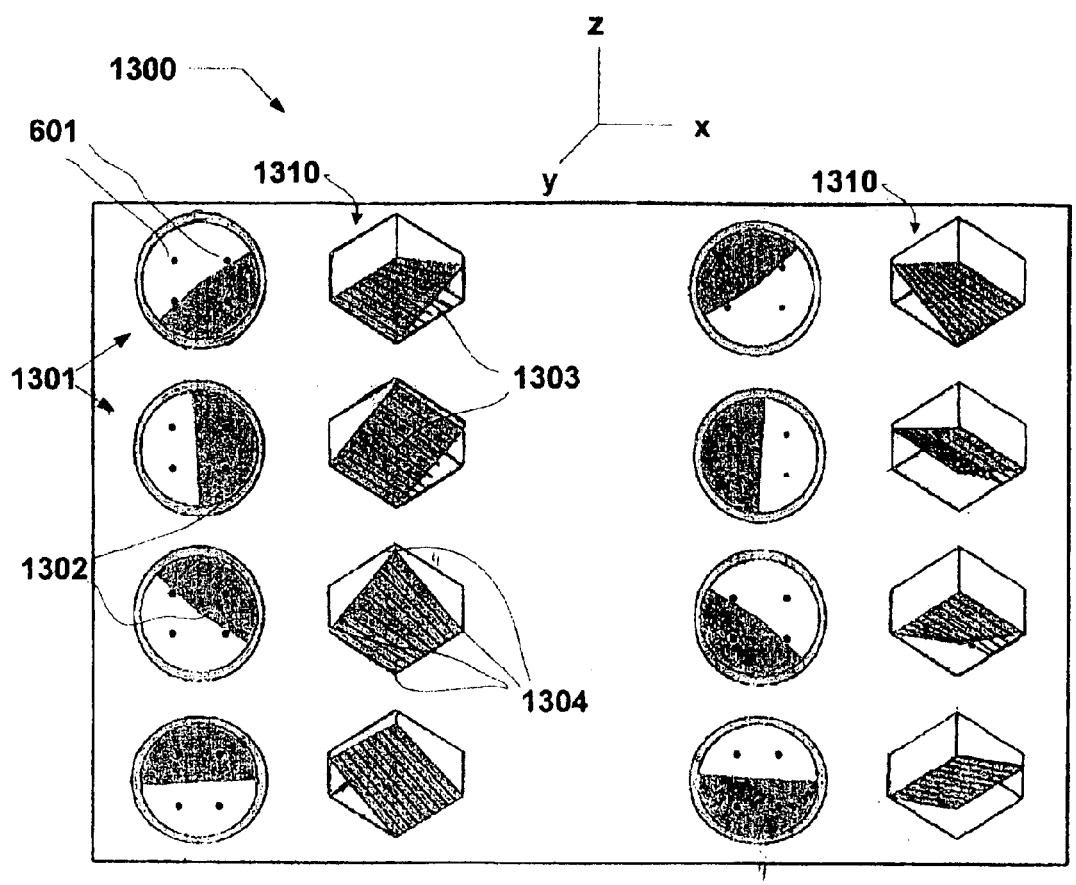
FIG. 13 presents a graphical presentation of a washover sequence tested at a laboratory scale, depicting representations of a top view of the test setup adjacent a 3D graph of processed data results.

Refer to FIGS. 6 and 13. FIG. 13 depicts a sequence 1300 of "snapshots" of dynamic washover from a test using the configuration of FIG. 6 in which the circular FIGS. 1301 represent a simulated top-view of the test cylinder 600 showing the relative position of the four washover sensors 601 in the array. The included shaded section 1302 in each circle 1301 represents the presence of fluid, in this case water, relative to the position of individual elements 601 in the sensor array. Each associated three-dimensional graph 1310 displays the actual acquired washover data. A value for each corner 1304 of the graph in the X-Y plane represents the location of an optical sensor (optical fiber termination) 601 and the value along the Z-axis represents a water depth of 0 to 1 cm (0.4"). The sensor array was calibrated by adding measured constant volumes of water to the cylinder 600 and recording the converted optical to electrical (O/E) voltage output of each of the four individual sensors 601.

Figure 14:
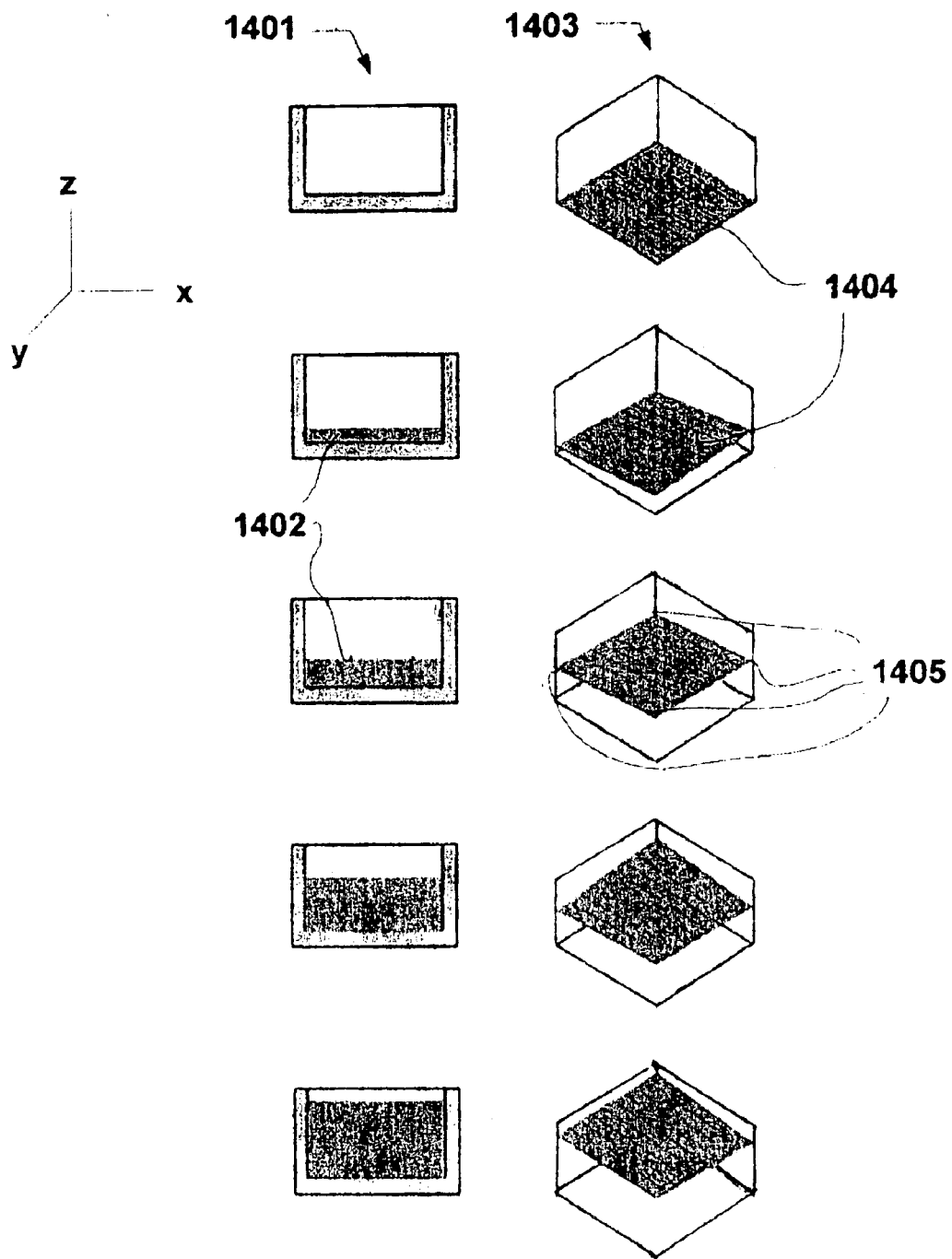
FIG. 14 depicts a way to view data from the test setup used also in FIG. 13, displaying a side view of a cross section of the cylinder used for multiple depths of water in the cylinder and associated data results as related to the multiple water depths in 3D graphs adjacent to each side view.

Refer to FIGS. 6 and 14. FIG. 14 shows a sequence from an experiment where the left column 1401 of figures represents a simulated side-view slice of the cylinder 600 of FIG. 6 with an increasing depth of water represented by the enclosed shaded rectangle 1402. The right column 1403 of FIG. 14 depicts a three-dimensional graph 1404 associated with each level, i.e., shaded rectangle 1402, in the left column 1401, displaying the actual water depth data acquired by the 4-sensor array of FIG. 6. Data related to each corner 1405 of the graph in the X-Y plane represents the location of an optical sensor (optical fiber termination) 601 while the Z-axis represents a value of water depth from 0 to 10 mm (0.4").

Figure 15:
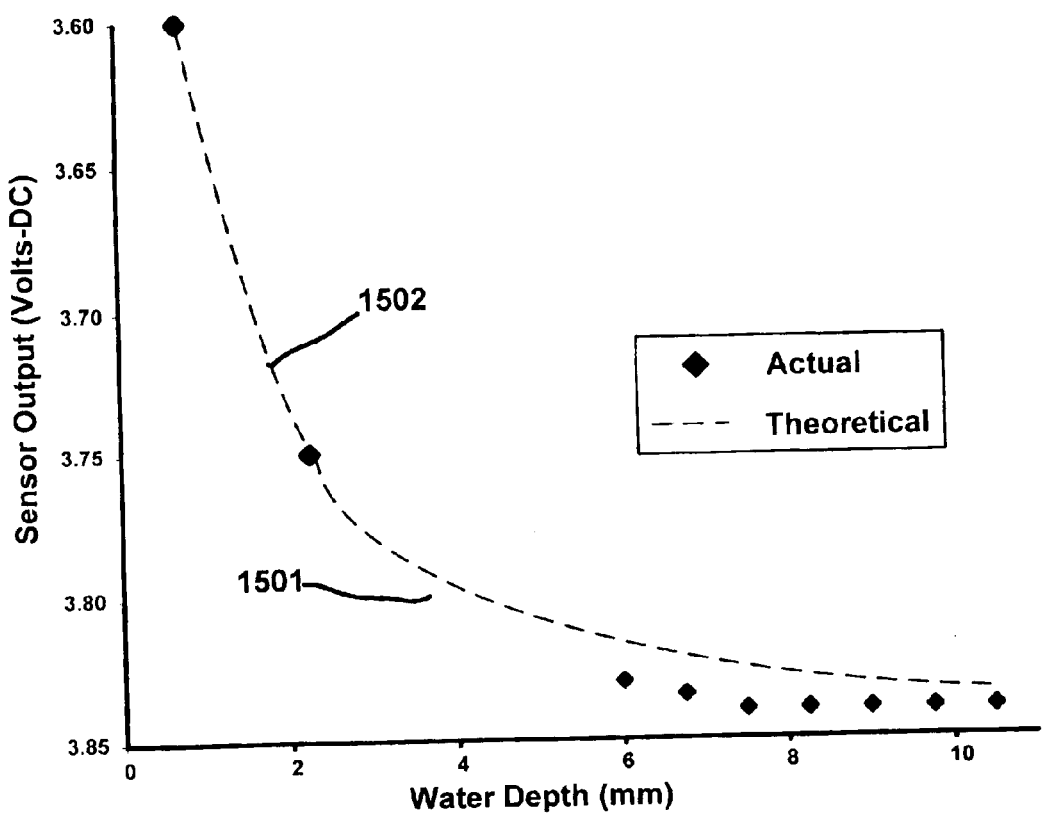
FIG. 15 depicts the relationship between measured sensor output (DC-voltage) and water depth from the laboratory setup of FIGS. 13 and 14, i.e., a calibration curve, as compared to the theoretica $1/r^2$ falloff relationship.

Refer to FIG. 15, the calibration curve 1501 from the above test. The ordinate is inverted to compensate for the inversion inherent in the output of the analog electronics 720 and to present data in a manner consistent with the theoretical $1/r^2$ falloff curve 1502 plotted as a reference.

To ensure that the system functioned under a variety of lighting conditions, tests were performed under natural skylight, incandescent light, fluorescent lighting, and in the dark. All lighting variations produced identical results.

Examples of Methods

Using basic concepts derived from optical transmission theory, multiple test instrumentation methodologies may be pursued. A photosensor 810 will "see" a different amount (magnitude) of light emanating from a remote, diffuse source such as ambient light or "natural sky light," depending on whether it is exposed to the light directly via ambient air or through a layer of another fluid, such as seawater. The effect of "seeing" through a layer of fluid is even more pronounced if, as with seawater, the fluid contains additional mineral and biologic elements that promote scattering and consequent attenuation of the received incident light.

Figure 16:
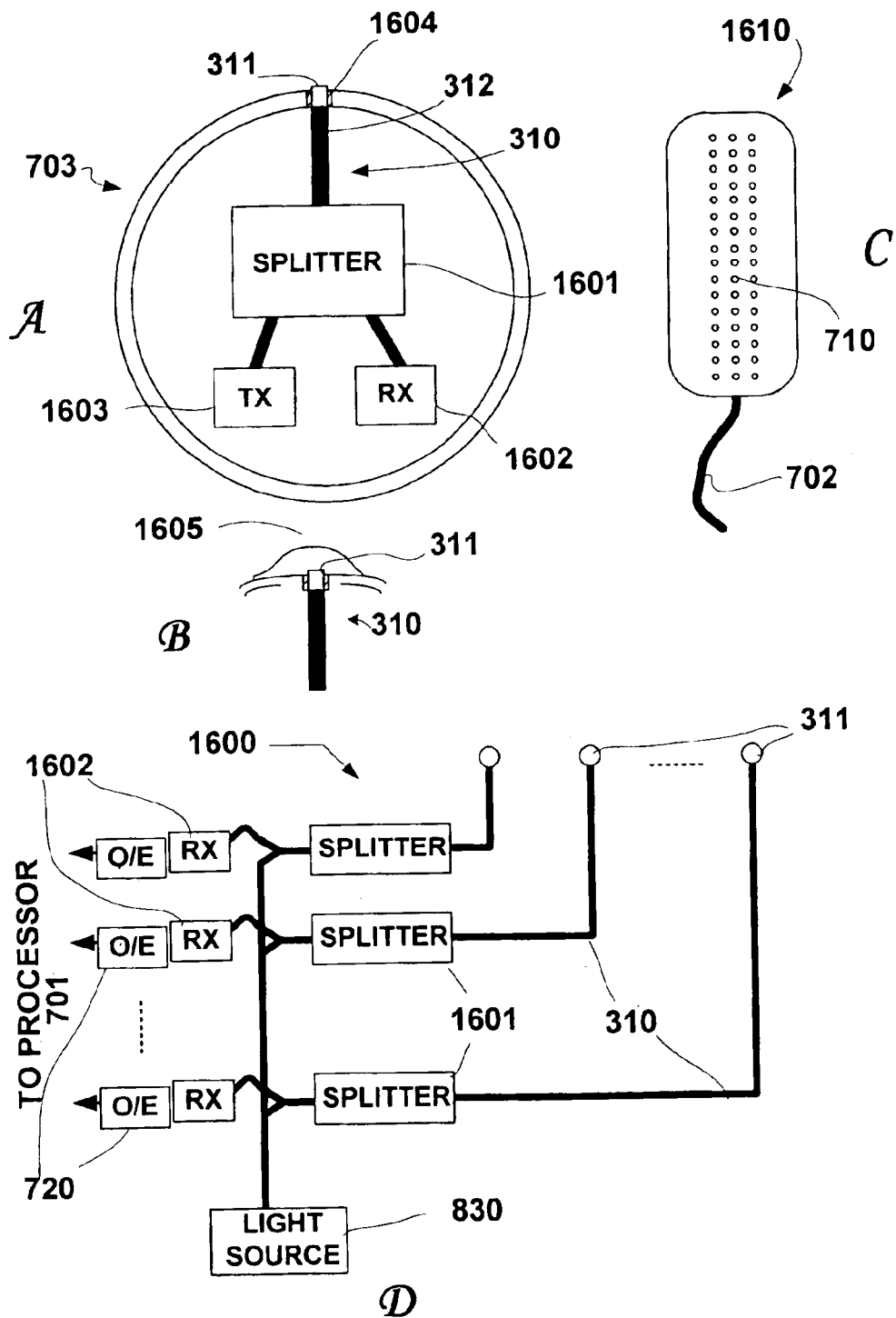
FIG. 16A depicts a single sensor as used in the reflectivity method of a preferred embodiment of the present invention.
FIG. 16B depicts the single sensor of FIG. 16A inundated with a fluid.
FIG. 16C depicts an array of sensors with umbilical that may be positioned on a thin conformal panel for use in a preferred embodiment of the present invention.
FIG. 16D is a block diagram of a preferred embodiment of the front end of a preferred embodiment of the present invention used with the reflectivity method.
Figure 17:
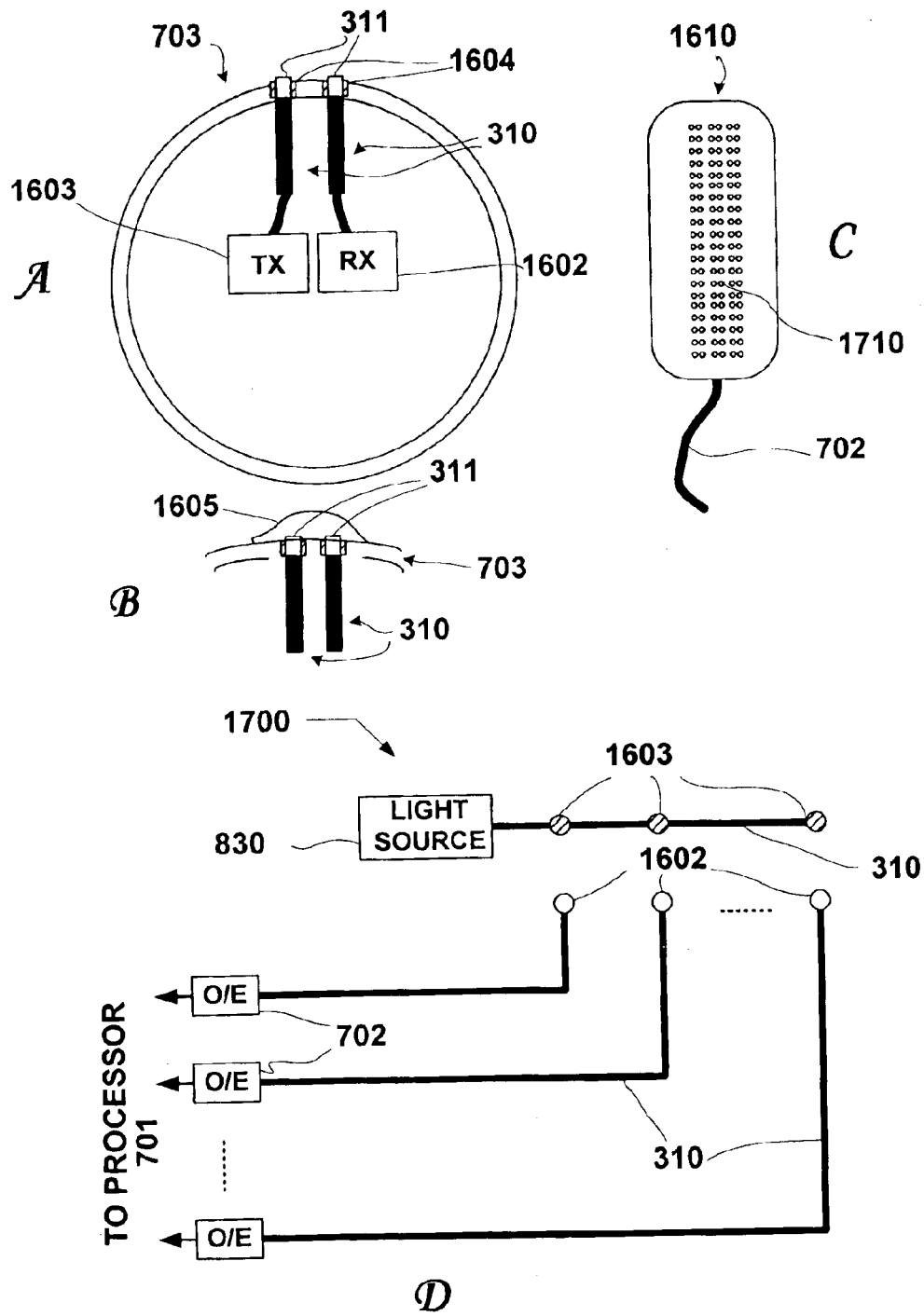
FIG. 17A depicts a single sensor pair as used in the cross-coupled method of a preferred embodiment of the present invention.
FIG. 17B depicts the single sensor pair of FIG. 17A inundated with a fluid.
FIG. 17C depicts an array of sensor pairs with umbilical that may be positioned on a thin conformal panel for use in a preferred embodiment of the present invention.
FIG. 17D is a block diagram of a preferred embodiment of the front end of a preferred embodiment of the present invention used with the cross-coupled method.

Refer to FIGS. 16 and 17. A layer of fluid "bridgin" (as at 1605 in FIG. 17B) an optical source/receiver pair 1602, 1603 may be sensed to provide indication of inundation 1605 of the surface of an object to which the receiver 1602 of the source/receiver pair 1602, 1603 is affixed. For example, a configuration may be established such that when the source/receiver pair 1602, 1603 is dry, the light from the source 1603 of the source/receiver pair 1602, 1603 is not coupled to the receiver 1602, but upon inundation 1605, the light may be coupled from source 1603 to receiver 1602 via one or more of the mechanisms of optical scattering, reflection, and refraction.

Using multiple optical fibers, there are three distinct optical washover implementations pursued in preferred embodiments of the present invention with variations of these also possible. These are: the "reflectivity method," the "cross-coupled method," and the "ambient illumination method."

Refer to FIG. 16. The reflectivity method uses an array 710 (FIG. 16C) of single point optical fiber (cable) terminations 311 (FIG. 16A), each termination 311 appearing flush with the surface of interest of the test object 703. Each termination 311 of the array 710 is connected to the converging port of an optical splitter 1601 (or circulator). An optical receiver (photosensor) 1602 is connected to one of the two diverging ports of the splitter 1601 and an optical source (transmitter) 1603 to the other. The receiver 1601, transmitter 1603, and splitter 1601 may be replaced with an optical power meter (not shown separately) that measures the reflected photonic power present in an optical fiber 310. The power meter monitors both the transmitted optical power and the reflected photonic power, producing a signal that is proportional to the normalized reflected photonic power.

The reflectivity method, as do the other two methods, monitors "fairly rapidly" changing reflectance levels at the end 311 of an optical fiber 310. It monitors the change in reflectivity at the boundary represented by the end 311 of the optical fiber 310 and its overlying material, be it ambient air, lake water, seawater, or any of a number of materials having a different reflectivity than that of the material representing the "normal" operating state for the optical fiber 310.

For example, if the optical fiber 310 as provided in an array 710 of FIG. 16C normally terminates in ambient air as shown in FIG. 16A, the reflectance will be known and established as the quiescent condition. Any deviation from this value indicates a different material (as illustrated at 1605 in FIG. 16B) is "covering" the optical fiber termination 311. Knowing the reflectance of a number of materials that could be expected to cover the optical fiber termination 311, one is able to determine instantaneously not only the state of the surface of the test object 703 at that termination 311 but also what is causing the change, e.g., snow, ice, seawater, steam, fog, etc. Using appropriate optical to electronic converters 720, wire connections (not shown separately except as an umbilical 702), and data processors, such as an appropriately configured PC 701, a real time display of the status of the test object 703 may be generated. As well, data may be recorded for later analysis, playback and display. Finally, a light source (transmitter) 830, as shown in the block diagram of FIG. 16D, may be modulated (as shown in FIG. 8 at 880) to assist in distinguishing unwanted (ambient) light from source light.

Refer to FIG. 16C. An array 710 need not be physically inserted into a test object 703 as described for FIG. 7, but may be configured on a thin flexible (conformable) panel 1610 that may be temporarily affixed to an object not specially configured for testing.

Refer to FIG. 17. As shown in FIG. 17A, the cross-coupled method uses two separate co-located optical path terminations 311 for each point in the array 1710, one a source 1603, the other a receiver (sensor) 1602. Transmission variation, also termed "cross-talk," is used to indicate a change in the material covering the pair of terminations 311. For example, to monitor washover of an object floating in a liquid, if the path between the two terminations 311 is dry, negligible cross-talk occurs, indicating the quiescent condition, i.e., no washover. Upon inundation of the two terminations 311, a "conducting bridge," as shown at 1605 of FIG. 17B, is formed over them, facilitating a cross-talk path. In a manner similar to the reflectivity method, knowing the magnitude of cross-talk caused by different "covering" materials 1605, allows one not only to monitor dry vs. wet conditions, for example, but also to determine the type of material covering the object 703. The same type of optical to electronic processors 720 and optical source 830 as used with the reflectivity method and shown in the block diagram of FIG. 17D may be used with this method, although splitters 1601 are not needed since data are taken from the receivers 1602 alone. Again, the array 1710 need not be permanently affixed to the object, but may be installed in a thin conformable panel 1610 as shown in FIG. 17C.

Figure 18:
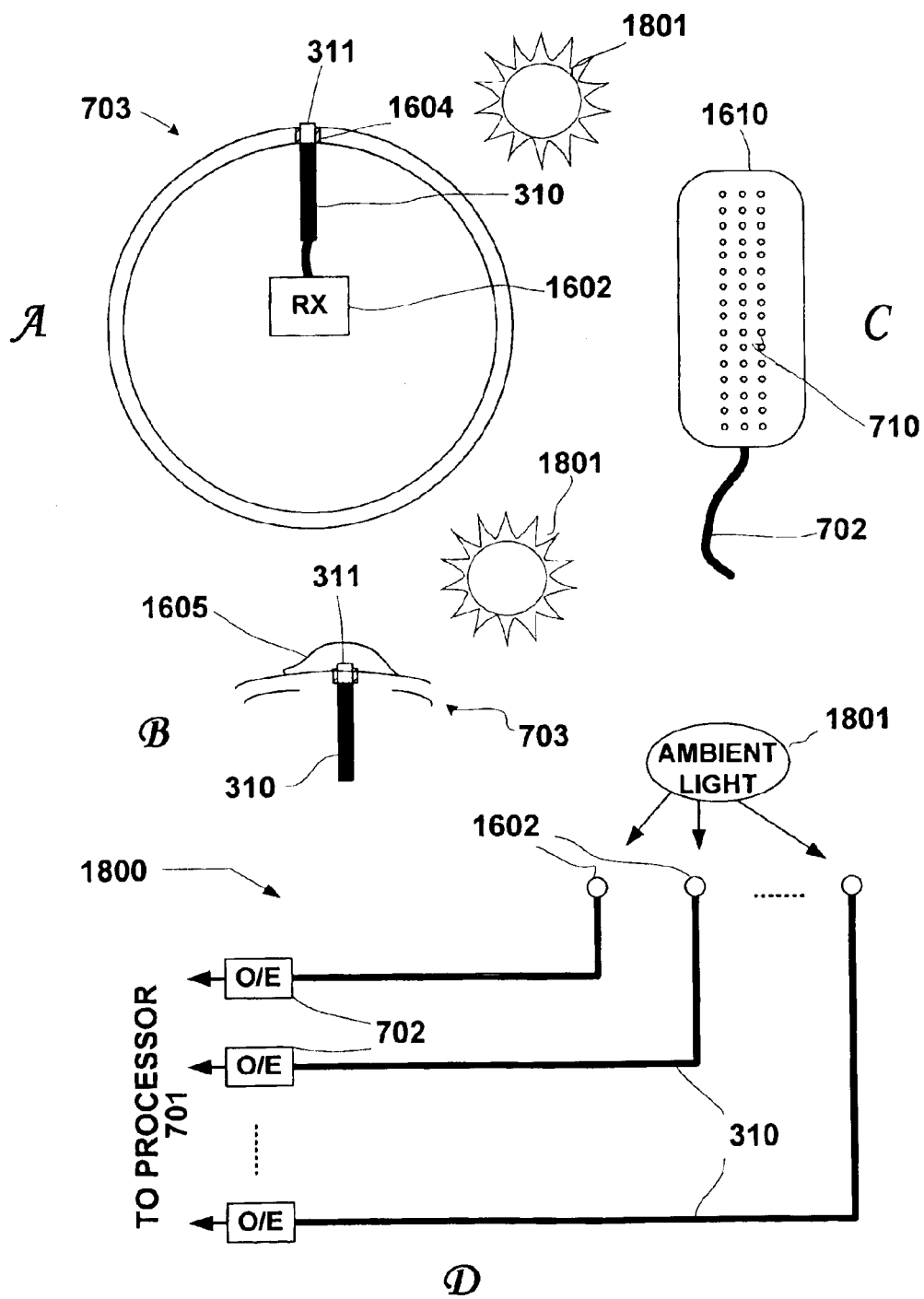
FIG. 18A depicts a single sensor as used in the ambient light method of a preferred embodiment of the present invention.
FIG. 18B depicts the single sensor of FIG. 18A inundated with a fluid.
FIG. 18C depicts an array of passive optical sensors with umbilical that may be positioned on a thin conformal panel for use in a preferred embodiment of the present invention.
FIG. 18D is a block diagram of a preferred embodiment of the front end of a preferred embodiment of the present invention used with the ambient light method.

Refer to FIG. 18. As shown in FIGS. 18A and 18C, the ambient illumination method relies on a single optical fiber end (sensor) 311 and a single photosensor (receiver) 1602 at each location within the array 710 affixed upon the test object 703. Again, the quiescent condition in the case of a washover sensor is the dry state. For a dry sensor array 710 illuminated by sunlight or other broad-beam light source 1801, all sensors read approximately the same level of photonic intensity. When washover occurs, some and possibly all of the sensors 311 will be inundated. While inundated, the sensor 311 receives less ambient light 1801 than when dry, thus indicating a covering exists, as shown in FIG. 18B at 1605. By sampling the received light at intervals pre-specified to yield appropriate dynamic information, one is able to "play back" what occurs during these events, either in real time or after some post-processing, or both, depending on the needs of the user. Again, as depicted in the block diagram of FIG. 18D, the same type of optical to electronic converters 720 may be used with this method as with the other two previously described methods.

Figure 19:
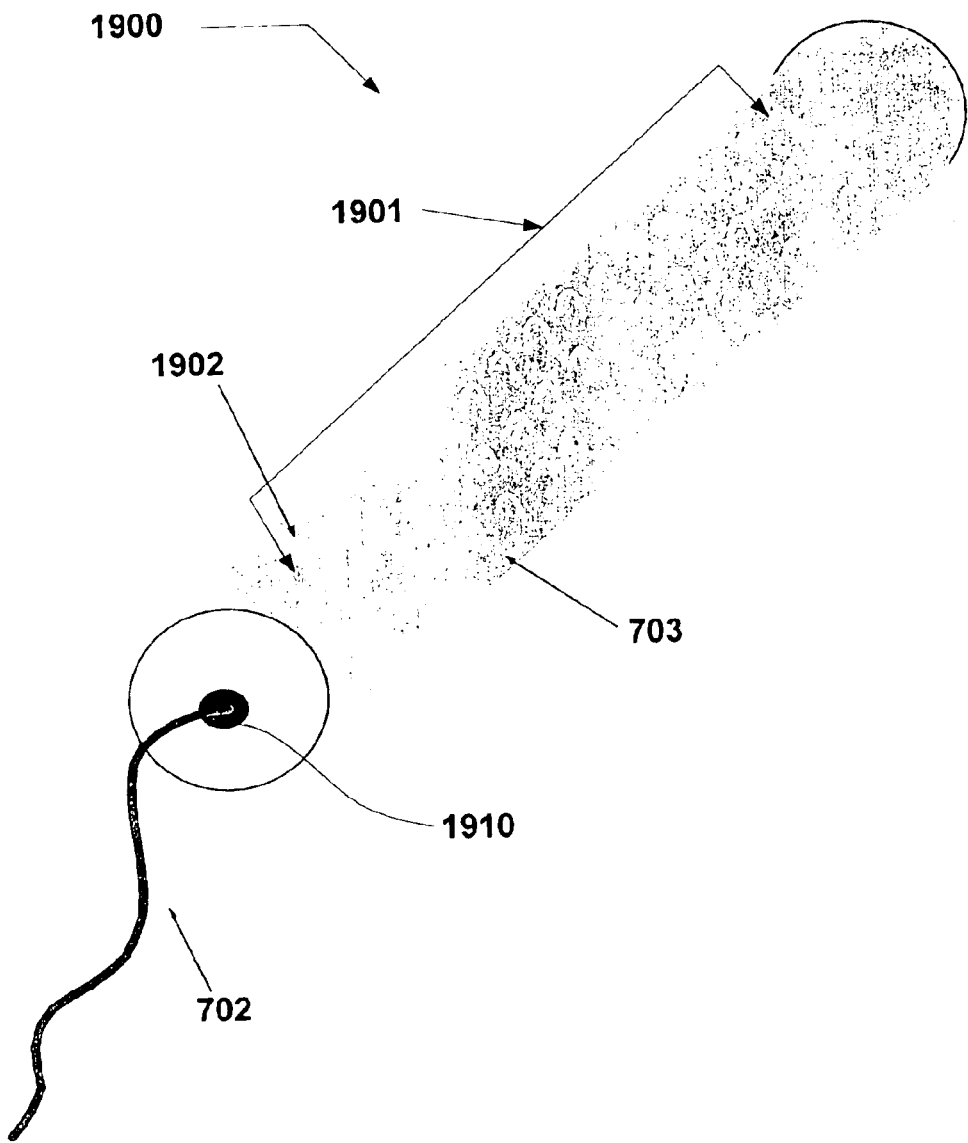
FIG. 19 depicts an array of optical sensors, exaggerated in relative dimension for illustration, that may be used on a test object as part of a preferred embodiment of the present invention.

Refer to FIGS. 7 and 19. For each of the above described methods, an umbilical 702, comprising either fiber optic cables (optical fibers) or hard wires, depending on implementation specifics, is arranged to lead from a watertight port 1910 on the test object 703 to a data processor, typically a multi-channel multiplexed data acquisition board interfaced to a personal computer 701 at a location remote from the test object 703, either onboard a vessel or on land. Using custom software, the PC 701 performs data acquisition, storage, processing, mapping, and display (visualization) functions, providing graphical, digital, and analog outputs as needed by a user.

Example of Distributed Sensor Configuration

The non-distributed test configurations for each of the methods described above are suitable for use in benign environments or for one-time setups such as employed in a laboratory to verify bench-scale models employing multiple open-ended optical fibers, i.e., one for each sensor. Additionally, in any practical embodiment, any of the non-distributed configurations require more expensive processors in that each must use a synchronized multiplexer to time division multiplex (TDM) the output of each of the individual sensors onto a single metallic or fiber transmission path for interconnection to a data acquisition system. This type of instrumentation may be available in a laboratory routinely, but robust versions for use in the field may prove to be an unnecessarily expensive burden as compared to distributed sensor systems.

In the present example, a method and instrumentation technique are employed with but a single optical fiber (cable) in communication with a series of "discrete" washover sensors. Refer to FIG. 19, illustrating the basic concept of a distributed fiber sensor array 1901 on an instrumented test object 703, where each of the inverted "U-shaped" features 1902 (exaggerated in size for illustrative purposes) represents a discrete sensor. The configuration 1900 employs the individual sensors 1902 as "bared" sections of a single optical fiber, i.e., a section of fiber optic cable extending between adjacent holes in the test object 703 has been stripped of its outer cladding to form each U-shaped sensor 1902. This single optical fiber 310 is "woven" through the outer surface of the test object 703 to form an array 1901 of sensors 1902, each sensor comprising a bared section of the single optical fiber 310 stretching between two holes on the external surface of the test object (or through a thin flat conformable panel as shown at 1610).

Figure 20:
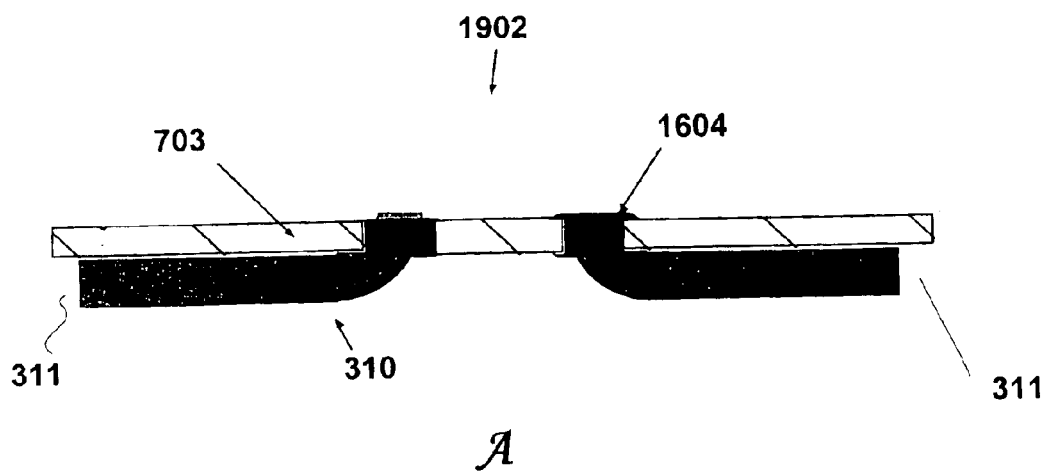
FIG. 20A depicts a side view of one of the optical sensors depicted in the array of FIG. 19 as installed in a test object.
FIG. 20B depicts a side view of the optical sensor depicted in FIG. 20A as installed nearly flush with the external surface of a test object.
Figure 20:
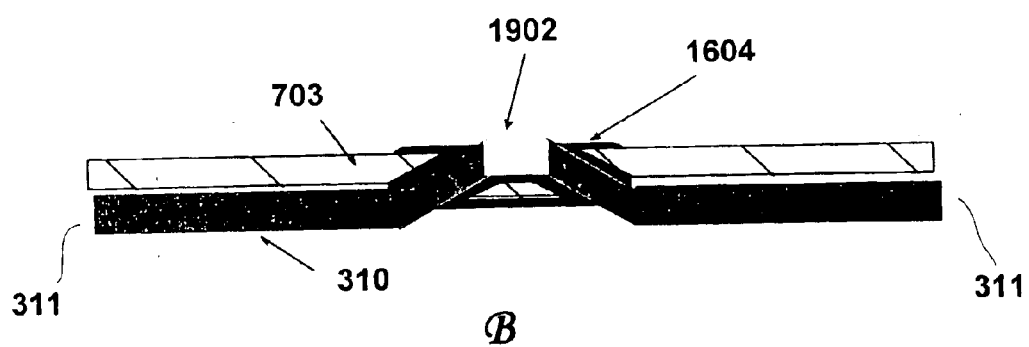

Refer to FIG. 20A, providing further detail on the U-shaped sensors 1902. In this embodiment, the individual sensors 1902 are discrete only in respect to their physical location, i.e., each U-shaped sensor 1902 is a part of a single optical fiber 310 with a central core 311. The optical fiber 310 is inserted through the outer skin of the test object 703, stripped of its external cladding, and the test object's skin is sealed from water intrusion by gaskets 1604 or caulking. Thus, the difference between the optical fiber 310 and the "discrete" sensor 1902 is the absence of opaque cladding where the sensor 1902 is exposed along the surface of the test object 703.

Refer to FIG. 20B. It is important to provide a small physical profile of the sensor 1902 upon the surface of the test object 703, thus, the configuration represented in FIG. 20B is a preferred embodiment where the optical fiber 310 is woven through the test object 703 to fit tightly against the skin of the test object 703, or even be recessed to fit flush with the surface. Another embodiment provides the same reduced profile as FIG. 20B but in a thin panel 1610 for temporary attachment to an object one does not wish to modify in order to test. Thus, for non-destructive testing (NDT), a thin panel 1610 may be "woven" as just described and affixed temporarily to the skin of an object that may be used later for its intended purpose, i.e., not just for testing. The thin panel 1610 may be less than 2.5 mm (0.1"), and bonded to the surface of interest with a strong but temporary adhesive. The umbilical 702 leads from the thin panel 1610, rather than from the interior of the test object 703 as is the case with previously described test configurations. This would provide a means for testing an object 703 without permanently altering its configuration, i.e., drilling holes through its external shell.

Figure 21:
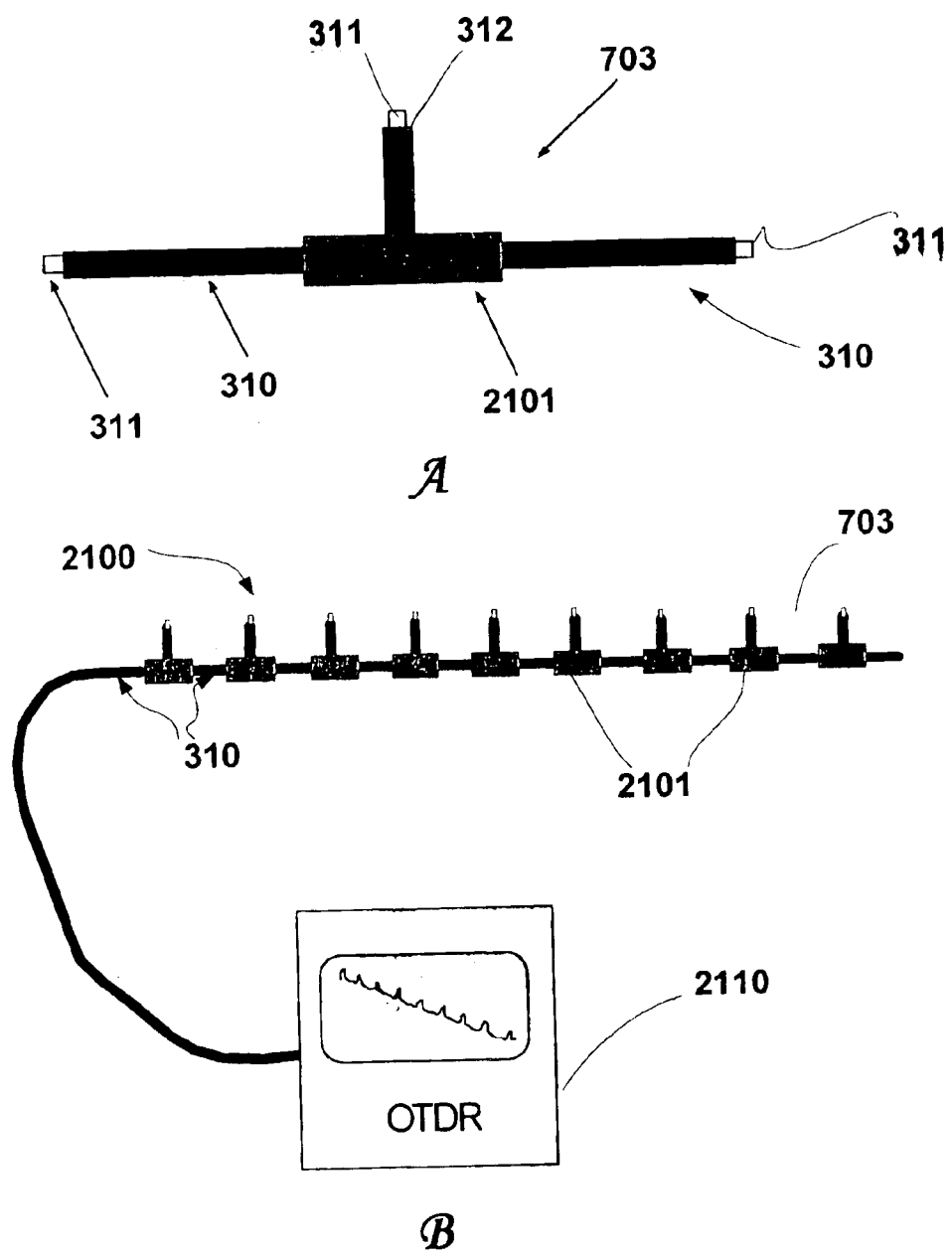
FIG. 21A depicts a single optical sensor provided from a T-connection off a single optical fiber transmission line.
FIG. 21B depicts a single row of optical sensors, each provided from a T-connection off a single optical fiber transmission line and their connection to a Optical Time Domain Reflectometer (OTDR).

Refer to FIGS. 7 and 21. An umbilical 702 provides two-way communication between an optical time domain reflectometer (OTDR) 2110 (not separately shown in FIG. 7) and a data processor/display such as a personal computer 701. This "distributed sensor system" 2100, here shown employing T-connectors 2101, acquires data and may map it in 3D, permitting visualization of washover in real-time using an OTDR 2110. It is important to note that while this system and technique are discussed in relation to the application of washover detection and mapping, there are numerous other military and commercial applications imaginable.

The principle of time domain reflectometry (TDR) is widely known, described in the technical literature, and applied to numerous measurements and testing applications. A light source, such as the LED 830 of FIG. 8, is coupled to the OTDR 2110, generating a very short duration light pulse, e.g., on the order of a nanosec. The OTDR in turn couples the light pulse to an optical fiber 310 that functions as a fiber-optic transmission line. That light pulse propagates down the optical fiber 310 at a fixed and calculable velocity that is a function of the speed of light, c, and the optical and physical characteristics of the optical fiber 310. The light pulse propagates until the end of the optical fiber 310 is reached and then is reflected back towards its source, i.e., the OTDR 2110. The time, t, in seconds, that it takes for the light pulse to make the round trip is given by:

$$t = \frac{2L}{v} \quad (16)$$

where:
L=length of the optical fiber (m)
v=velocity of propagation of the light pulse (m/s)
The propagation velocity is given by:

$$v = \frac{c}{\eta} \quad (17)$$

where:
c=velocity of light in free space, $3 \times 10^8$ M/s
and
$\eta$=index of refraction of the media surrounding the optical fiber.

Figure 22:
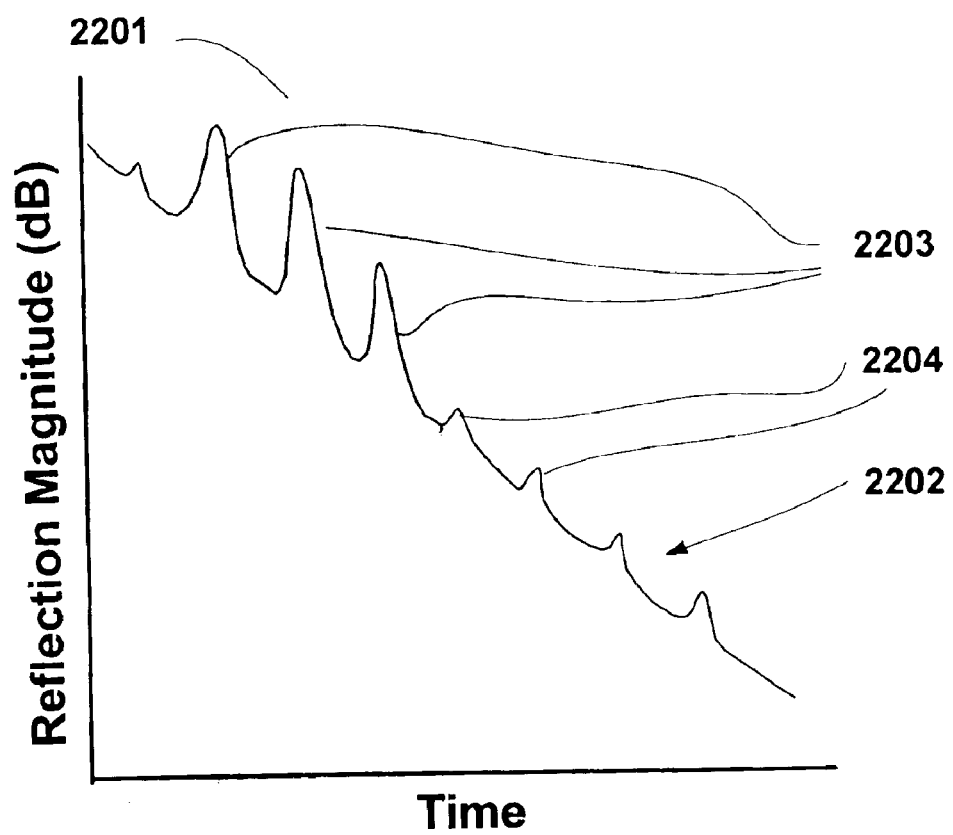
FIG. 22 shows the single row of optical sensors of FIG. 21B aligned beneath a trace, exaggerated for illustrative purposes, presented on the OTDR display used in a preferred embodiment of the present invention.
Figure 22:
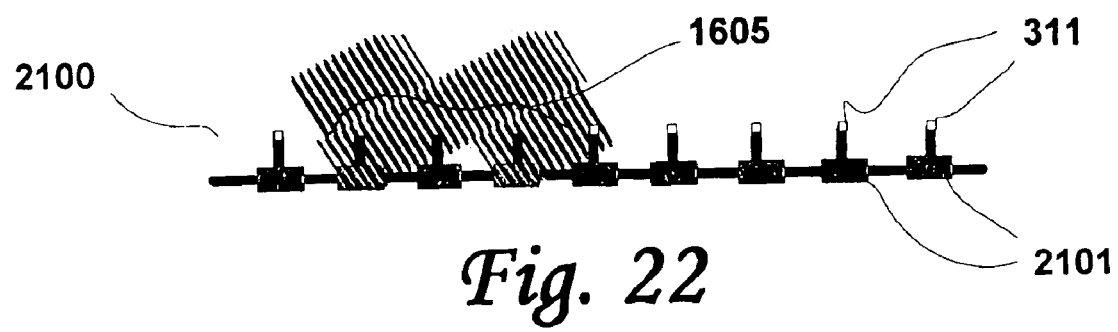

Refer to FIGS. 21 and 22. A distributed fiber optic sensor array 2100 or system employs serial connections of fiber optic sensors 311 distributed along a single fiber optic cable (transmission path) 310. This concept is discussed in depth in Udd (1990). The application of OTDR with a distributed fiber optic sensor 311 is discussed in Allard (1990). An optical fiber 310 may be configured in such a manner to include numerous discrete sensors 311 distributed uniformly, or by some other advantageous distribution, along its entire length. The index of refraction contrast at each discrete sensor 311 is caused by the insertion of that sensor 311 at points along the length of the optical fiber 310. This causes a small reflective pulse 2204 to appear on the OTDR trace 2202 for each of the sensors 311 so inserted. Under quiescent conditions, e.g., "washover" sensors 311 exposed only to ambient air, these pulses 2204 are of minimal amplitude. When the environment surrounding a sensor 311 changes, e.g., the sensor 311 is inundated by seawater 1605, the reflection coefficient at the sensor/environment boundary changes causing a pulse 2203 present on the display associated with the OTDR 2110 to change magnitude.

At any change of the environment about an individual sensor 311 along the optical fiber 310, e.g., from optical fiber/air 301 to optical fiber/water 302, a refractive index contrast (or discontinuity) exists. As a light pulse traveling down the optical fiber 310 from the light source 830 used with the OTDR 2110 encounters these changed sensor conditions, a portion of the energy in the pulse of light is reflected back to the source 2110 from the discontinuity. A portion of the energy continues to propagate through the optical fiber 310 until another boundary discontinuity such as a discrete sensor 311, is encountered or the end of the optical fiber 310 causes all or part of the remaining energy to return along the optical fiber 310 to the source 2110. Measuring the round trip "time of flight" of the pulse along the optical fiber 310 permits calculation of the physical distance from the OTDR source 2110 to each of the discrete optical sensors 311 encountered. Knowledge of the refractive index of the optical sensor component 311 and the surrounding medium, e.g., air or water, facilitates calculation of a reflection coefficient, $\rho$. The value of $\rho$ provides an indication of the environment to which the individual optical sensor 311 is exposed, e.g., wet or dry. The relative magnitude of the reflection is proportional to the reflection coefficient, $\rho$, as defined in Eqn. (3) above, and some small, often inconsequential, attenuation at the sensor 311 due to the distance of the sensor 311 from the OTDR source 2110.

The length of the optical fiber 310 and number of discrete sensors 311 able to be included is a function of the calculated maximum transmission losses. The far (distal) end (not shown separately) of the optical fiber 310 may be terminated either in a reflection-free termination (not shown separately) or left open. By keeping the optical fiber 310 open ended, a mismatch reflection will occur and be visible on the OTDR 2110 display. Having this mismatch reflection present is useful to indicate the location of the distal end of the optical fiber 310 in relation to the array 2100 of distributed sensors 311.

The near (proximal) end of the optical fiber 310 may extend up to several hundred meters as part of an "umbilical" (not shown separately) to connect to an OTDR 2110 beyond the test object 703. In practical applications any umbilical such as that umbilical 702 to and from the test object 703 to the processor(s) 701, 720 should be strain-relieved and armored.

Refer to FIG. 22, illustrating how a distributed sensor 2100 incorporating T-connectors 2101 functions and how the associated OTDR trace 2202 may appear when sensors 311 are covered, e.g., wet 1605, as highlighted in the shaded area 2201 and when sensors 311 are dry as indicated by pulses 2204 of minimal amplitude. A linear array 2100 of fiber optic sensors 311 is partially covered in water 1605. Sensors 311 surrounding the wetted sensors (not visible under the washover 1605 of FIG. 22) are dry.

The OTDR trace 2202 shows a reflection pulse 2203, 2204 representative of each one of the sensors 311 in the optical array 2100. Sensors 311 that are wet with washover as represented by the cross-hatched area 1605, exhibit a larger magnitude pulse 2203 than pulses 2204 from dry sensors 311. The general slope (exaggerated for illustration) of the trace 2202 is due to linear attenuation with distance from the source (associated with the OTDR 2110) along the optical fiber 310. This attenuation is usually referenced in decibels (dB) per length, e.g., dB/km. The general slope of the trace (curve) 2202 is proportional to loss due to attenuation. For a short array 2100, e.g., less than 10 m, this loss is negligible and the slope approaches zero. The maximum length of the optical fiber 310 and maximum number of included discrete sensors 311 is a function of the maximum transmission path attenuation encountered and the sensitivity of the OTDR 2110 employed. The minimum spacing between discrete sensors 311 is a function of the selected pulse width. A narrower pulse width permits closer placement of distributed sensors 311 along a given length of optical fiber 310 and provides greater detail about washover geometry. As first discussed above, the distributed sensor 2100 also may be implemented in a flexible, reusable, conformal sensor panel 1610 that would not require drilling holes in an object 703 to be tested while still minimizing disruption of washover geometry at the surface of its application to the object 703.

While the invention has been described in terms of its preferred embodiments, one skilled in the art will recognize that the invention may be practiced with modifications within the spirit and scope of the appended claims. For example, although the system is described in specific examples for mapping, visualizing, or imaging washover, it may operate on any surface and in conditions that one would wish to map occurrences on a surface. For example, although the system is described in specific examples for mapping, visualizing, or imaging washover, it may operate on any surface and in conditions that one would wish to map occurrences on a surface, such as drifting snow, drifting sand or silt, sediment, etc., both in a practical implementation and in a scaled experimental testing facility such as a wind tunnel, wave tank, etc. It may be suitable for other applications such as determining operating conditions in a manufacturing plant, e.g., calibrating the process establishing the thickness and uniformity of a transparent or semi-transparent polishing liquid use on a silicon wafer for purposes of optimizing polishing, quality sampling the process for layering a transparent coating of sugar on a confection, etc. Further, monitoring 3-D depth of any transparent or semi-transparent film of molten wax, oil or liquid plastic in a wave-coating tank may be another possibility.

Thus, it is intended that all matter contained in the foregoing description or shown in the accompanying drawings shall be interpreted as illustrative rather than limiting, and the invention should be defined only in accordance with the following claims and their equivalents.

The abstract is provided to comply with the rules requiring an abstract, which will allow a searcher to quickly ascertain the subject matter of the technical disclosure of any patent issued from this disclosure. It is submitted with the understanding that it will not be used to interpret or limit the scone or meaning of the claims, 37 CFR § 1.72(b). Any advantages and benefits described may not apply to all embodiments of the invention.

I claim:

1. A system for dynamically capturing interaction of an object with its environment, comprising:
   at least one array of fiber optic sensors affixed approximately conformally to at least part of a surface of said object,
   wherein said array is configured to provide a pre-specified level of detail of said interaction via at least receipt of optical signals reflected from the boundary formed by said sensors and said environment, and
   wherein said sensor operates in at least one pre-specified range of the visible, IR, and UV spectra;
   at least one path in operable communication with said sensor; and
   a data collection, processing, recording and display sub-system in operable communication with said paths,
   wherein said sub-system collects data representing sampling of at least one optical characteristic resultant from said receipt, processes said data, and captures selected said processed data for real time display as well as for future use, and wherein said sub-system at least measures changes in reflectivity of said reflected optical signals at the boundary between said sensors and said environment.

2. The system of claim 1 in which said at least one optical characteristic is selected from the group consisting of: wavelength, pulse width, amplitude, phase, phase shift, modulation, and any combination thereof.

3. The system of claim 1 in which said array is mounted approximately conformally on said object to enable exposure of said sensors to at least one external surface of said object.

4. The system of claim 1 in which said sensors comprises at least one exposed section on at least one optical fiber,
wherein said optical fiber incorporates cladding along unexposed lengths of said optical fiber and no cladding along each said exposed section, and
wherein said optical fiber also incorporates at least part of said path.

5. The system of claim 1 in which each said sensor comprises an exposed section of a single optical fiber,
wherein said single optical fiber incorporates cladding along unexposed lengths of said optical fiber and no cladding along each said exposed section, and
wherein said single optical fiber incorporates said path.

6. The system of claim 1 in which said data collection, processing, recording and display sub-system comprises:
at least one signal converter for converting at least one optical frequency to at least one radio frequency;
at least one multi-channel multiplexed data acquisition printed circuit board incorporating at least one analog-to-digital converter; and
at least one personal computer, incorporating a display, in operable communication with said at least one multi-channel multiplexed data acquisition printed circuit board.

7. The system of claim 6 further comprising software loadable on said at least one personal computer for implementing at least some processing of said data.

8. The system of claim 1 further employing a light source separate from ambient light.

9. The system of claim 8 in which said light source is selected from the group consisting of: LEDs, lasers, non-coherent light sources, and any combination thereof.

10. The system of claim 8 in which said light source is pulsed at a pre-specified pulse width and pulse repetition frequency.

11. The system of claim 8 in which said light source is modulated by a pre-specified technique.

12. The system of claim 1 in which said arrays are at least one distributed sensor array and said system further incorporates at least one optical time domain reflectometer (OTDR).

13. The system of claim 1 further incorporating at least one umbilical from said object to said data collection, processing, recording and display sub-system,
wherein said umbilical carries said data collected from said array to said subsystem, and
wherein said umbilical may provide electromagnetic energy from said sub-system to said arrays.

14. The system of claim 1 further comprising at least one optical splitter associated with each said fiber optic sensor, in which:
each said sensor is a discrete optical fiber in operable communication with said optical splitter, said optical splitter incorporating at least one optical receiver and at least one optical transmitter;
wherein said optical splitter separates signals to be associated with said receiver from signals to be associated with said transmitter, and
each said optical splitter is in operable communication with said sub-system via a synchronized time division multiplexer (TDM), and
each said discrete optical fiber receives light energy from a light source in operable communication with said optical splitter,
wherein said discrete optical fiber detects changes in reflectivity at the boundary represented by said sensor and any material overlying said boundary, said material to include ambient air.

15. The system of claim 1 in which each said sensor is represented by a pair of optical fibers that are cross-coupled in operation, said pair employing two separate optical path terminations such that cross-talk between said optical fibers of said pair indicates a change in material covering said pair, in which:
a first of said pair is a transmitter optical fiber obtaining light energy from a source in operable communication with said data collection, processing, recording and display sub-system via a synchronized time division multiplexer (TDM), and
a second of said two optical fibers is a receiver optical fiber in operable communication with said data collection, processing, recording and display via said synchronized time division multiplexer (TDM).

16. The system of claim 1 in which:
each said sensor of said array is represented by the exposed end of a discrete optical fiber; and
each said exposed end is illuminated by an ambient source of broadband light that may vary within a known limited range,
wherein each said discrete optical fiber detects approximately the same level of photonic intensity when operating in a pre-specified quiescent state, and
wherein upon at least partial instantaneous covering of said exposed ends with a material, said discrete optical fiber receives less ambient light than when uncovered; and
each said optical fiber is in operable communication with said sub-system via a synchronized time division multiplexer (TDM).

17. The system of claim 1 in which said object is suspended in a fluid and a part of said object is not in contact with said fluid under ore-specified conditions.

18. The system of claim 17 in which said fluid is water and said object is a towed body.

19. A method for dynamically capturing data from reflections of optical signals at boundaries with optical sensors to estimate the interaction of an object with its environment, comprising:
providing at least one array of fiber optic sensors;
affixing said array approximately conformally to at least a part of a surface of said object,
via said array, collecting as data at least one said reflection;
processing said collected data to derive at least one characteristic of said reflections;
recording selected said processed data; and
displaying selected said processed data.

20. The method of claim 19 in which said characteristics are selected from the group consisting of: wavelength, pulse width, amplitude, phase, phase shift, modulation, and any combination thereof.

21. The method of claim 19 suspending said object in a fluid such that a part of said object is not in contact with said fluid under pre-specified conditions.

22. The method of claim 21 providing said fluid as water and said object as a towed body.

23. A simulator for dynamically capturing interaction of an object with its environment, comprising:
- a model of said object;
- at least one array of fiber optic sensors affixed approximately conformally to at least a part of a surface of said model, wherein said array is configured to provide a pre-specified level of detail of said interaction via at least receipt of optical signals reflected from the boundary formed by said sensors and said environment, and wherein said sensors operates in at least one pre-specified range of the visible, IR, and UV spectra;
- at least one path in operable communication with each said sensor; and
- a data collection, processing, recording and display sub-system in operable communication with said paths, wherein said sub-system collects data representing sampling of at least one optical characteristic resultant from said receipt, processes said data, and captures selected said processed data for real time display as well as for future use, and wherein said sub-system at least measures changes in reflectivity of said reflected optical signals at the boundary between said sensors and said environment.

24. A system for detecting, measuring and capturing interaction of an object with the environment encompassing said object, to include displaying a representation of said interaction in real time, comprising:
- at least one array of optical sensors affixed to measure said interaction over at least part of a surface of interest of said object, wherein said optical sensors in a given said array comprise exposed sections of the same optical fiber, and wherein said same optical fiber incorporates cladding along unexposed lengths of said same optical fiber and no cladding along said exposed sections, and wherein said arrays are configured to provide a pre-specified level of detail of said interaction, and wherein each said optical sensor operates in at least one pre-specified range of the visible, IR, and UV spectra;
- at least one optical path in operable communication with each said optical sensor wherein said same optical fiber serves as said path for communicating optical signals to and from said array in which said same optical fiber comprises said optical sensors of that said array; and
- a data collection, processing, recording and display sub-system in operable communication with said at least one optical path, wherein said data collection, processing, recording and display sub-system collects data representing the sampling of at least one optical characteristic resultant from any said interaction as detected by said optical sensors, processes said data, and captures selected said data for real time display as well as for future use.

25. The system of claim 24 in which said data collection, processing, recording and display sub-system comprises:
- at least one signal converter for converting at least one optical frequency to at least one radio frequency;
- at least one multi-channel multiplexed data acquisition printed circuit board incorporating at least one analog-to-digital converter; and
- at least one personal computer, incorporating a display, in operable communication with said at least one multi-channel multiplexed data acquisition printed circuit board.

26. The system of claim 24 further comprising software loadable on said at least one personal computer for implementing at least some processing of said data.

27. The system of claim 24 in which said object is a towed body only part of which is in communication with water in which said towed body is suspended when said water is quiescent.

28. A system for detecting, measuring and capturing interaction of an object with the environment encompassing said object, to include displaying a representation of said interaction in real time, comprising:
- at least one synchronized time division multiplexer (TDM);
- at least one optical splitter incorporating at least one optical receiver and at least one optical transmitter, said splitters in operable communication with at least one said time division multiplexer (TDM);
- at least one array of optical sensors affixed to measure said interaction over at least part of a surface of interest of said object, in which:
  - each said sensor of said array of optical sensors is represented by a discrete optical fiber in operable communication with at least one said optical splitters, wherein said optical splitter separates signals to be associated with said incorporated optical receiver from signals to be associated with said incorporated optical transmitter;

each said discrete optical fiber receives light energy from a source in operable communication with at least one said optical splitters, wherein each said discrete optical fiber detects changes in reflectivity at the boundary represented by said sensor and any material overlying said boundary, to include ambient air and any of a number of materials having a different reflectivity than that of a material representing a pre-specified quiescent operating state for said sensor, wherein said arrays are configured to provide a pre-specified level of detail of said interaction, and wherein each said optical sensor operates in at least one pro-specified range of the visible, IR, and UV spectra;
- at least one optical path in operable communication with each said optical sensor; and
- a data collection, processing, recording and display sub-system in operable communication with said at least one optical path, wherein each said optical splitter is in operable communication with said data collection, processing recording and display sub-system via at least one said synchronized time division multiplexer (TDM), and wherein said data collection, processing, recording and display sub-system collects data representing the sampling of at least one optical characteristic resultant from any said interaction as detected by said optical sensors, processes said data, and captures selected said data for real time display as well as for future use.

29. The system of claim 28 in which each said discrete optical fiber is illuminated by an ambient source of broadband light that may vary within a known limited range, wherein each said discrete optical fiber reads approximately the same level of photonic intensity as any other said discrete optical fiber in said array when operating in a pre-specified quiescent state, and wherein upon at least partial instantaneous covering of said discrete optical fiber with a material, said discrete optical fiber receives less ambient light than when uncovered.

30. A system for detecting, measuring and capturing interaction of an object with the environment encompassing said object, to include displaying a representation of said interaction in real time, comprising:

at least one optical path;

at least one synchronized time division multiplexer (TDM) in operable communication with at least one said optical path;

a data collection, processing, recording and display sub-system in operable communication with said at least one optical path, at least one array of optical sensors affixed to measure said interaction over at least part of a surface of interest of said object, in which each said sensor comprises a pair of optical fibers that are cross-coupled in operation, said pair employing two separate optical path terminations such that cross-talk between said optical fibers of said pair indicates a change in material covering said pair, wherein a first optical fiber of said pair is a transmitter optical fiber that obtains light energy from a source in operable communication with said data collection, processing, recording and display sub-system via at least one said synchronized time division multiplexer (TDM), and wherein a second optical fiber of said pair is a receiver optical fiber in operable communication with said data collection, processing, recording and display via at least one said synchronized time division multiplexer (TDM), and wherein said pair of optical fibers detects changes in reflectivity at the boundary represented by said sensor and any material overlying said boundary, to include ambient air and any of a number of materials having a different reflectivity than that of a material representing a pre-specified quiescent operating state for said sensor, and wherein each said optical fiber is in operable communication with at least one said optical paths; and wherein said arrays are configured to provide a pre-specified level of detail of said interaction, and wherein each said optical sensor operates in at least one pre-specified range of the visible, IR, and UV spectra, and wherein said data collection, processing, recording and display sub-system collects data representing the sampling of at least one optical characteristic resultant from any said interaction as detected by said optical sensors, processes said data, and captures selected said data for real time display as well as for fixture use.

31. The system of claim 30 in which each said optical sensor is illuminated by an ambient source of broadband light that may vary within a known limited range, wherein each said optical sensor reads approximately the same level of photonic intensity as any other said optical sensor in said array when operating in a pre-specified quiescent state, and wherein upon at least partial instantaneous covering of said discrete optical sensor with a material, said discrete optical fiber receives less ambient light than when uncovered.

32. A method for detecting, measuring and capturing interaction of a towed body with the water in which it is being towed, to include displaying a representation of said interaction in real time, comprising:

providing at least one array of optical sensors affixed to measure said interaction over at least part of a surface of interest of said towed body, via said at least one array of optical sensors, collecting as data at least one optical characteristic of said interaction;

processing said collected data;

recording selected said processed data; and displaying selected said processed data, wherein said data may be displayed in at least one format as said representation.

* * * * *